(12) United States Patent
Srinivasan et al.

(10) Patent No.: US 10,550,107 B2
(45) Date of Patent: Feb. 4, 2020

(54) PROCESS FOR THE PREPARATION OF N-[4-[(3-CHLORO-4-FLUORO PHENYL) AMINO]-7-[[(3S-TETRAHYDRO-3-FURANYL]OXY]-6-QUINAZOLINYL]-4-(DIMETHYL AMINO)-(2E)-2-BUTENAMIDE (2Z)-2-BUTENEDIOATE (1:2) AND ITS POLYMORPHS THEREOF

(71) Applicant: MSN LABORATORIES PRIVATE LIMITED, Hyderabad, Telangana (IN)

(72) Inventors: Thirumalai Rajan Srinivasan, Telangana (IN); Eswaraiah Sajja, Telangana (IN); Venkata Panakala Rao Gogulapati, Telangana (IN); Rajesham Boge, Telangana (IN)

(73) Assignee: MSN LABORATORIES PRIVATE LIMITED, Hyderabad, Telangana (IN)

( * ) Notice: Subject to any disclaimer, the term of this patent is extended or adjusted under 35 U.S.C. 154(b) by 140 days.

(21) Appl. No.: 15/575,778

(22) PCT Filed: May 11, 2016

(86) PCT No.: PCT/IN2016/000123
§ 371 (c)(1),
(2) Date: Sep. 10, 2018

(87) PCT Pub. No.: WO2016/185485
PCT Pub. Date: Nov. 24, 2016

(65) Prior Publication Data
US 2018/0297989 A1 Oct. 18, 2018

(30) Foreign Application Priority Data

May 18, 2015 (IN) .......................... 2476/CHE/2015
Oct. 16, 2015 (IN) .......................... 5555/CHE/2015

(51) Int. Cl.
C07D 407/12 (2006.01)
C07D 405/12 (2006.01)
B01D 9/00 (2006.01)

(52) U.S. Cl.
CPC ........... C07D 405/12 (2013.01); B01D 9/005 (2013.01)

(58) Field of Classification Search
CPC ..................................................... C07D 407/12
See application file for complete search history.

(56) References Cited

FOREIGN PATENT DOCUMENTS

| CA | 02841960 | 1/2014 |
|---|---|---|
| CN | 103254183 | 8/2013 |
| CN | 104447713 | 3/2015 |
| CN | 104478863 | 4/2015 |
| CN | 104540820 | 4/2015 |
| WO | WO 2014/183560 | 11/2014 |

OTHER PUBLICATIONS

International Search Report issued in International Patent Application No. PCT/IN2016/000123, dated Nov. 21, 2016.

Primary Examiner — Bruck Kifle
(74) Attorney, Agent, or Firm — IP Pundit LLC

(57) ABSTRACT

The present invention relates to an improved process for the preparation of N-[4-[(3-chloro-4-fluorophenyl)amino]-7-[[(3S)-tetrahydro-3-furanyl]oxy]-6-quinazolinyl]-4-(dimethyl amino)-(2E)-2-butenamide (2Z)-2-butenedioate (1:2) represented by the following structural formula:

Formula-1

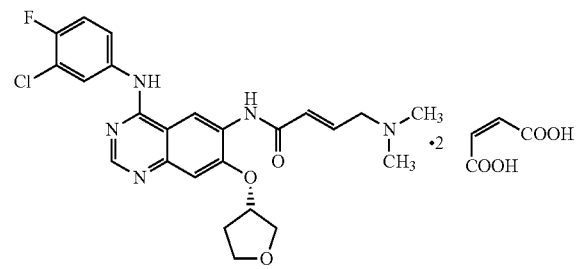

20 Claims, 6 Drawing Sheets

PROCESS FOR THE PREPARATION OF N-[4-[(3-CHLORO-4-FLUORO PHENYL) AMINO]-7-[[(3S-TETRAHYDRO-3-FURANYL]OXY]-6-QUINAZOLINYL]-4-(DIMETHYL AMINO)-(2E)-2-BUTENAMIDE (2Z)-2-BUTENEDIOATE (1:2) AND ITS POLYMORPHS THEREOF

This application is a national phase application under 35 U.S.C. § 371 of International Application No. PCT/IN2016/000123, filed on May 11, 2016, which claims priority to claims the benefit of priority of our Indian patent application number 2476/CHE/2015 filed on 18 May 2015 and 5555/CHE/2015 filed on Oct. 16, 2015; the disclosure of which are incorporated herein by reference in its entirety.

FIELD OF THE INVENTION

The present invention relates to an improved process for the preparation of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) represented by the following structural formula:

Formula-1

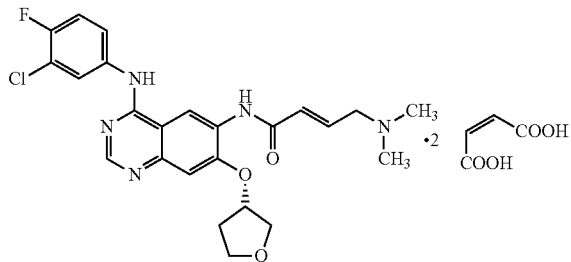

The present invention also provides novel crystalline forms of 4-[(3-chloro-4-fluorophenyl) amino]-6-amino-7-((S)-tetrahydrofuran-3-yloxy)-quinazoline dihydrochloride compound of formula-8a and N-[4-[(3-chloro-4-fluorophenyl)amino]-7-[[(3S)-tetrahydro-3-furanyl]oxy]-6-quinazolinyl]-4-(dimethylamino)-(2E)-2-butenamide(2Z)-2-butenedioate (1:2) compound of formula-1 and its process for the preparation.

Further, the present invention relates to an amorphous N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1 and its process for preparation.

BACKGROUND OF THE INVENTION

N-[4-[(3-chloro-4-fluorophenyl)amino]-7-[[(3S)-tetrahydro-3-furanyl]oxy]-6-quinazolinyl]-4-(dimethylamino)-(2E)-2-butenamide, is commonly known as Afatinib.

N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) is commonly known as Afatinib dimaleate.

Afatinib is investigational orally administered irreversible inhibitor of both the epidermal growth factor receptor (EGFR) and human epidermal receptor 2 (HER2) tyrosine kinases. Afatinib is marketed as Afatinib dimaleate under the brand names Gilotrif in the United States and Giotrif in Europe.

Afatinib or its pharmaceutically acceptable salt was first generically disclosed in U.S. Pat. No. 6,251,912 and specifically disclosed in U.S. Pat. No. RE43,431.

U.S. Pat. No. 8,426,586 B2, WO2013052157 A1 and IPCOM000240150D described various crystalline forms of Afatinib dimaleate.

U.S. Pat. No. RE43,431 discloses process for the preparation of 2-butenamide, N-[4-[(3-chloro-4-fluorophenyl)amino]-7-[[(3S)-tetrahydro-3-furanyl]oxy]-6-quinazolinyl]-4-(dimethylamino)-, (2E)-, (2Z)-2-butenedioate (1:2). The said patent also discloses one pot process for the preparation of 2-butenamide, N-[4-[(3-chloro-4-fluorophenyl)amino]-7-[[(3S)-tetrahydro-3-furanyl]oxy]-6-quinazolinyl]-4-(dimethylamino). The disclosed process involves treatment of bromocrotonic acid with oxalyl chloride and N,N-dimethylformamide in methylene chloride to form crude bromocrotonic acid chloride, which is further treated with (S)—N-(3-chloro-4-fluorophenyl)-7-(tetrahydrofuran-3-yloxy) quinazoline-4,6-diamine in tetrahydrofuran followed by treatment with N,N-dimethylamine to afford 2-butenamide, N-[4-[(3-chloro-4-fluorophenyl)amino]-7-[[(3S)-tetrahydro-3-furanyl]oxy]-6-quinazolinyl]-4-(dimethylamino) free base with less yield. Further it was purified by column chromatography, which is a laborious and time consuming process and also it is not suitable for commercial scale purpose.

Hence, there is a need in the art to develop an improved, economically viable and efficient, simple process for the preparation of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) with high yield and purity.

Polymorphism, the occurrence of different crystal forms, is a property of some molecules and molecular complexes. A single molecule may give rise to a variety of polymorphs having same molecular formula and distinct physical properties like melting point, solubility profiles, thermal behaviors (e.g. measured by thermo gravimetric analysis—"TGA", or differential scanning calorimetry—"DSC"), X-ray powder diffraction (XRPD or powder XRD) pattern, infrared absorption fingerprint, and solid state nuclear magnetic resonance (NMR) spectrum. Polymorphic forms of a compound can be distinguished in a laboratory by X-ray diffraction spectroscopy and by other methods such as, infrared spectrometry and differential scanning calorimetry. Solvent medium and mode of crystallization play very important role in obtaining a polymorphic form over the other.

Discovering new polymorphic forms and solvates of a pharmaceutical product can provide materials having desirable processing properties, such as ease of handling, ease of processing, storage stability, ease of purification or as desirable intermediate crystal forms that facilitate conversion to other polymorphic forms.

New polymorphic forms and solvates of a pharmaceutically useful compound or salts thereof can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, or improved shelf-life. For at least these reasons, there is a need for additional solid state forms or polymorphs of compound of formula-1.

BRIEF DESCRIPTION OF THE INVENTION

The first aspect of the present invention is to provide an amorphous Afatinib dimaleate.

The second aspect of the present invention is to provide a process for the preparation of amorphous Afatinib dimaleate.

The third aspect of the present invention is to provide an alternate process for the preparation of amorphous Afatinib dimaleate.

The fourth aspect of the present invention is to provide pure amorphous N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1 and its process for the preparation.

The fifth aspect of the present invention is to provide amorphous solid dispersion comprising N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1 and at least one pharmaceutically acceptable excipient.

The sixth aspect of the present invention is to provide a process for the preparation of amorphous solid dispersion comprising N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1 and at least one pharmaceutically acceptable excipient.

The seventh aspect of the present invention relates to a novel crystalline form of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1, hereinafter designated as crystalline Form-M.

The eighth aspect of the present invention present invention is to provide a process for the preparation of crystalline form-M of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1.

The ninth aspect of the present invention relates to another, novel crystalline form of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1, hereinafter designated as crystalline form-S.

The tenth aspect of the present invention is to provide a process for the preparation of crystalline form-S of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1.

The eleventh aspect of the present invention is to provide an improved process for the preparation of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1.

The twelfth aspect of the present invention is to provide a novel crystalline form of 4-[(3-Chloro-4-fluorophenyl)amino]-6-amino-7-((S)-tetrahydrofuran-3-yloxy)-quinazoline dihydrochloride compound of formula-8a, hereinafter designated as crystalline form-M.

The thirteenth aspect of the present invention is to provide a process for the preparation of crystalline form-M of 4-[(3-Chloro-4-fluorophenyl)amino]-6-amino-7-((S)-tetrahydrofuran-3-yloxy)-quinazoline dihydrochloride compound of formula-8a.

The fourteenth aspect of the present invention is to provide another novel crystalline form of 4-[(3-Chloro-4-fluorophenyl)amino]-6-amino-7-((S)-tetrahydrofuran-3-yloxy)-quinazoline dihydrochloride compound of formula-8a, hereinafter designated as crystalline form-N.

The fifteenth aspect of the present invention is to provide a process for the preparation of crystalline form-N of 4-[(3-Chloro-4-fluorophenyl)amino]-6-amino-7-((S)-tetrahydrofuran-3-yloxy)-quinazoline dihydrochloride compound of formula-8a.

The sixteenth aspect of the present invention is to provide a process for the preparation of N-[4-[(3-chloro-4-fluorophenyl)amino]-7-[[(3S)-tetrahydro-3-furanyl]oxy]-6-quinazolinyl]-4-(dimethylamino)-(2E)-2-butenamide compound of formula-10.

The seventeenth aspect of the present invention is to provide a novel crystalline form of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1, hereinafter designated as crystalline form-R.

The eighteenth aspect of the present invention is to provide a process for the preparation of novel crystalline form-R of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1.

BRIEF DESCRIPTION OF THE DRAWINGS

FIG. 10: Illustrates the PXRD pattern of crystalline Form-M of 4-[(3-Chloro-4-fluorophenyl)amino]-6-amino-7-((S)tetrahydrofuran-3-yloxy)-quinazoline dihydrochloride compound of formula-8a.

FIG. 11: Illustrates the PXRD pattern of crystalline Form-N of 4-[(3-Chloro-4-fluoro phenyl)amino]-6-amino-7-((S)tetrahydrofuran-3-yloxy)-quinazoline dihydrochloride compound of formula-8a.

DETAILED DESCRIPTION OF THE INVENTION

Figure 1:
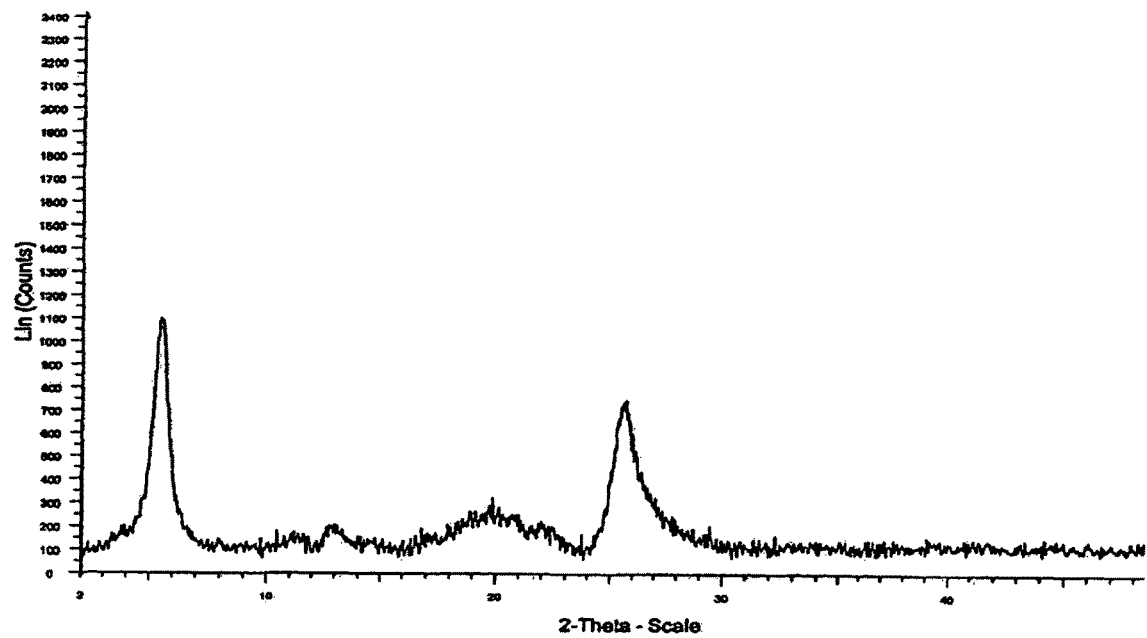
FIG. 1: Illustrates the powder X-ray diffraction pattern of amorphous Afatinib dimaleate.

The term "suitable solvent" used in the present invention includes, but not limited to "ester solvents" such as ethyl acetate, methyl acetate, isopropyl acetate, n-butyl acetate and the like; "ether solvents" such as tetrahydrofuran, dimethyl ether, diethyl ether, diisopropyl ether, methyl tert-butyl ether, 1,4-dioxane and the like; "hydrocarbon solvents" such as toluene, hexane, heptane, pet ether, benzene, xylene, cyclohexane and the like; "polar aprotic solvents" such as dimethyl acetamide, dimethylsulfoxide, N,N-dimethylformamide, N-methyl-2-pyrrolidone, nitromethane, nitroethane and the like; "ketone solvents" such as acetone, methyl ethyl ketone, methyl isobutyl ketone and the like; "alcoholic solvents" such as methanol, ethanol, n-propanol, isopropanol, n-butanol, isobutanol, tert-butanol and the like; "chloro solvents" such as dichloromethane, chloroform, dichloroethane, carbon tetrachloride and the like; "nitrile solvents" such as acetonitrile, butyronitrile, isobutyronitrile and the like; "protic solvent" such as acetic acid; "polar solvent" such as water or mixtures thereof.

"Lyophilization" is also called freeze-drying. Lyophilization is a process which converts water from a frozen state to a gaseous state without going through a liquid state. This process removes moisture from the cells of specimens while the specimens remain frozen.

The term "amorphous" refers to a solid without long-range crystalline order. The amorphous form of the present invention preferably contains less than about 10% crystalline forms, more preferably less than 5% crystalline forms, and still more preferably less than 1% or is essentially free of crystalline forms. "Essentially free of crystalline forms" means that no crystalline polymorph forms can be detected within the limits of an X-ray Powder Diffractometer.

The term "solid dispersion" refers to a system in a solid state comprising at least two components, wherein one component is dispersed throughout the other component or components. In the present invention, one component of solid dispersion is active pharmaceutical ingredient such as N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) and other component is a pharmaceutically acceptable excipient.

The term "base" used herein the present invention until unless specified is selected from inorganic bases like "alkali metal hydroxides" such as lithium hydroxide, sodium hydroxide, potassium hydroxide and the like; "alkali metal carbonates" such as sodium carbonate, potassium carbonate, lithium carbonate, cesium carbonate and the like; "alkali metal bicarbonates" such as sodium bicarbonate, potassium bicarbonate, lithium bicarbonate, cesium bicarbonate and the like; "alkali metal hydrides" such as sodium hydride, potassium hydride, lithium hydride and the like; "alkali metal alkoxides" such as sodium methoxide, sodium ethoxide, sodium tert-butoxide, potassium methoxide, potassium ethoxide, potassium tert-butoxide and the like; ammonia; and organic bases such as triethyl amine, methyl amine, ethyl amine, 1,8-Diazabicyclo[5.4.0]undec-7-ene (DBU), Tetra-n-butylammonium fluoride (TBAF), 1,5-Diazabicyclo (4.3.0)non-5-ene (DBN), lithium dioisoporpylamide (LDA), n-butyl lithium, tribenzylamine, isopropyl amine, diisopropylamine, diisopropylethylamine, N-methylmorpholine, N-ethylmorpholine, piperidine, dimethylaminopyridine, morpholine, pyridine, 2,6-lutidine, 2,4,6-collidine, imidazole, 1-methylimidazole, 1,2,4-triazole, 1,4-diazabicyclo[2.2.2]octane (DABCO) or mixtures thereof.

The suitable "reducing agent" is selected from Lithium aluminum hydride (LiAlH4), hydroquinone, sodium amalgum, diborane, sodium borohydride, lithium borohydride, iron-acetic acid, iron-hydrochloric acid, compounds containing the $Sn^{+2}$ ion such as tin(II)chloride, sulfite compounds, hydrazine, zinc-mercury amalgum, diisobutylaluminum hydride (DIBAL-H), Lindlar catalyst and the like.

The term "acid" used in the present invention refers to inorganic acid selected from hydrochloric acid, hydrobromic acid, sulfuric acid, nitric acid, phosphoric acid, sulfamic acid and the like; organic acid such as formic acid, acetic acid, trifluoro acetic acid, methane sulfonic acid, ethane sulfonic acid, benzene sulfonic acid, trifluoromethane sulfonic acid, p-toluene sulfonic acid, tartaric acid, mandelic acid, malic acid, oxalic acid, formic acid, ascorbic acid, phosphorous acid, maleic acid, succinic acid, malonic acid, oxalic acid, dibenzoyl tararic acid, lactic acid, cinnamic acid and the like.

The first aspect of the present invention provides an amorphous Afatinib dimaleate. Further, the amorphous Afatinib dimaleate is characterized by its powder X-ray diffraction pattern as shown in FIG. 1.

The second aspect of the present invention provides a process for the preparation of amorphous Afatinib dimaleate, comprising of:
  a) Dissolving Afatinib dimaleate in a suitable solvent,
  b) isolating the amorphous Afatinib dimaleate from the solution of step-(a).
Wherein,
  in step-a) the suitable solvent is selected from ester solvents, ether solvents, nitrile solvents, alcoholic solvents, hydrocarbon solvents, polar aprotic solvent, chloro solvents, ketone solvents and polar solvents,
  in step-b) the isolation of amorphous Afatinib dimaleate involves removal of solvent by the techniques such as lyophilization, spray drying, recrystallization, quench cooling the melt, rapid solvent evaporation, slow solvent evaporation, anti-solvent addition, slurry recrystallization, crystallization from the melt and desolvation etc.

In a preferred embodiment of the present invention provides a process for the preparation of amorphous Afatinib dimaleate, comprising of:
  a) Dissolving the Afatinib dimaleate in water,
  b) lyophilizing the amorphous Afatinib dimaleate from the solution of step-(a).

The third aspect of the present invention is to provide a process for the preparation of amorphous Afatinib dimaleate, comprising of:
  a) Adding maleic acid to a mixture of Afatinib and a suitable solvent,
  b) stirring the reaction mixture to obtain a clear solution,
  c) isolating the amorphous Afatinib dimaleate from the solution of step-(b).
wherein,
  in step-a) the suitable solvent is selected from ester solvents, ether solvents, nitrile solvents, alcoholic solvents, hydrocarbon solvents, polar aprotic solvent, chloro solvents, ketone solvents and polar solvents;
  in step-c) the isolation of amorphous Afatinib dimaleate involves removal of solvent by the techniques such as lyophilization, spray drying, recrystallization, quench cooling the melt, rapid solvent evaporation, slow solvent evaporation, anti-solvent addition, slurry recrystallization, crystallization from the melt and desolvation etc.

A preferred embodiment of the present invention provides a process for the preparation of amorphous Afatinib dimaleate, comprising of:

a) Adding maleic acid to a mixture of Afatinib and water,
b) stirring the reaction mixture to get clear solution,
c) lyophilizing the amorphous Afatinib dimaleate from the solution of step-(b).

Figure 2:
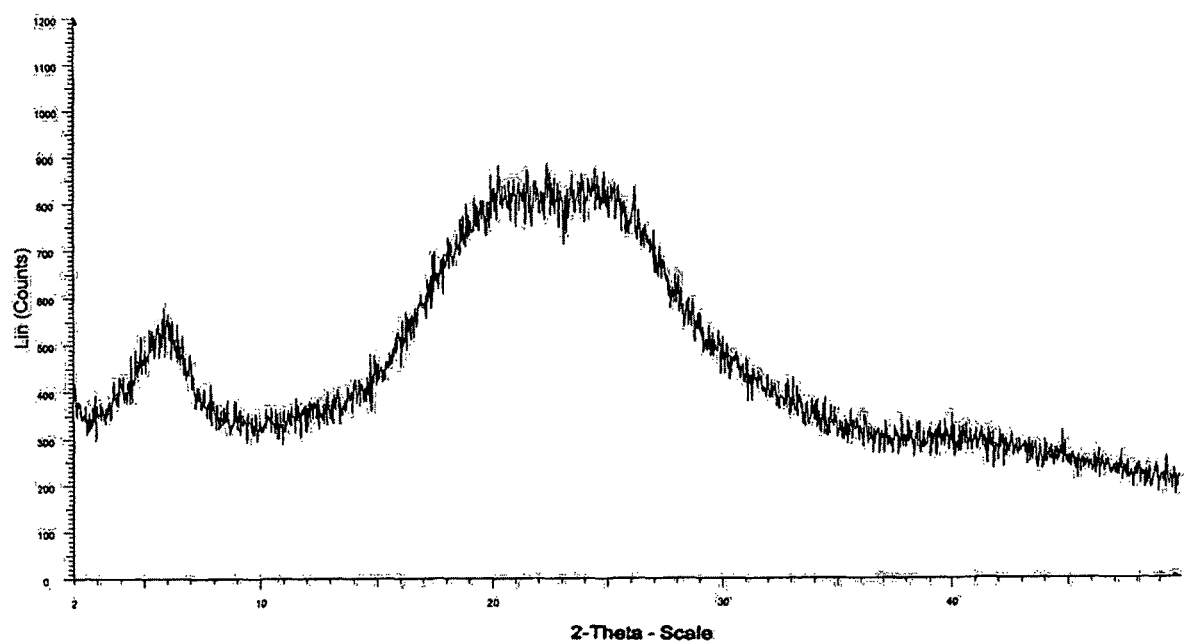
FIG. 2: Illustrates the powder X-ray diffraction pattern of pure amorphous form of compound of formula-1 prepared in accordance with example-1.

The fourth aspect of the present invention provides pure amorphous N-[4-[(3-chloro-4-fluorophenyl)amino]-7-[[(3S)-tetrahydro-3-furanyl]oxy]-6-quinazolinyl]-4-(dimethyl amino)-(2E)-2-butenamide (2Z)-2-butenedioate (1:2) compound of formula-1 which is characterized by its powder X-ray diffraction pattern as shown in FIG. 2.

Further, the fourth aspect of the present invention also provides a process for the preparation of pure amorphous compound of formula-1, which comprises of:
  a) Dissolving the compound of formula-1 in a suitable solvent or mixture of solvents,
  b) removing the solvent(s) from the reaction mixture and drying the material to get pure amorphous compound of formula-1.

Wherein, the suitable solvent used in step-(a) can be selected from hydrocarbon solvents, ether solvents, ester solvents, polar-aprotic solvents, chloro solvents, ketone solvents, nitrile solvents, alcohol solvents, polar solvents, formic acid, acetic acid, alkyl ethers of ethylene glycol or propylene glycol or their mixtures; the compound of formula-1 may be dissolved in a suitable solvent by heating the reaction mixture to a suitable temperature ranges from 0° C. to 150° C.;

After dissolving the compound of formula-1 in the solvent system, the solution may optionally be treated with charcoal or any other suitable material to remove color and/or to clarify the solution;

Optionally, the solution obtained above may be filtered to remove any insoluble particles. The solution may be filtered by passing through paper, glass fiber or other membrane material or a bed of a clarifying agent such as Celite® or hyflow. Depending upon the equipment used and the concentration and temperature of the solution, the filtration apparatus may need to be preheated to avoid premature crystallization.

In step-b) suitable techniques which may be used for the removal of solvent from the reaction mixture includes but not limited to evaporation, evaporation under reduced pressure, flash evaporation, vacuum drying, concentrating the reaction mixture, atmospheric distillation, vacuum distillation, distillation by using a rotational distillation device such as a Buchi Rotavapor, agitated thin film drying, melt extrusion, spray drying, freeze drying (lyophilization), spray-freeze drying, addition of suitable anti-solvent to the reaction mixture followed by filtration of the precipitated solid, cooling the clear solution to lower temperatures to precipitate the solid followed by filtration of the reaction or by any other suitable techniques known in the art.

In a preferred embodiment of the present invention provides a process for the preparation of pure amorphous compound of formula-1, which comprising of:
  a) Dissolving the compound of formula-1 in methanol,
  b) distilling off the solvent from the reaction mixture under reduced pressure and drying to get pure amorphous compound of formula-1.

The fifth aspect of the present invention provides amorphous solid dispersion comprising of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1 and at least one pharmaceutically acceptable excipient.

In general, the pharmaceutically acceptable excipient is selected from but not limited to polyvinylpyrrolidone (povidone or PVP; PVP of different grades like K-15, K-30, K-60, K-90 and K-120 may be used), polyvinylpolypyrrolidone, polysorbate, cross linked polyvinyl pyrrolidone (crospovidone), Eudragit, polyethylene glycol (macrogol or PEG), polyvinyl alcohol, polyvinyl chloride, polyvinyl acetate, propylene glycol, cellulose, cellulose acetate phthalate (CAP), methyl cellulose, carboxymethyl cellulose (CMC, its sodium and calcium salts), carboxymethylethyl cellulose (CMEC), ethyl cellulose, hydroxymethyl cellulose, ethyl hydroxyethyl cellulose, hydroxyethylcellulose, hydroxypropyl cellulose (HPC), hydroxypropyl cellulose acetate succinate, hydroxypropyl methyl cellulose (hypromellose or HPMC), hydroxypropyl methylcellulose acetate succinate (HPMCAS), hydroxyethyl methyl cellulose succinate (HEMCS), hydroxypropyl cellulose acetate succinate (HPCAS), hydroxypropyl methylcellulose phthalate (HPMC-P), hydroxypropyl methylcellulose acetate phthalate, microcrystalline cellulose (MCC), cross linked sodium carboxymethyl cellulose (croscarmellose sodium), cross linked calcium carboxymethyl cellulose, magnesium stearate, aluminium stearate, calcium stearate, magnesium carbonate, talc, iron oxide (red, yellow, black), stearic acid, dextrates, dextrin, dextrose, sucrose, glucose, xylitol, lactitol, sorbitol, mannitol, maltitol, maltose, raffinose, fructose, maltodextrin, anhydrous lactose, lactose monohydrate, starches such as maize starch or corn starch, sodium starch glycolate, sodium carboxymethyl starch, pregelatinized starch, gelatin, sodium dodecyl sulfate, edetate disodium, sodium phosphate, sodium lauryl sulfate, triacetin, sucralose, calcium phosphate, polydextrose, α-, β-, γ-cyclodextrins, sulfobutylether beta-cyclodextrin, sodium stearyl fumarate, fumaric acid, alginic acid, sodium alginate, propylene glycol alginate, citric acid, succinic acid, carbomer, docusate sodium, glyceryl behenate, glyceryl stearate, meglumine, arginine, polyethylene oxide, polyvinyl acetate phthalates and the like.

In the present invention, the ratio of the amount by weight of compound of formula-1 within the solid dispersion to the amount by weight of the excipient therein ranges from but not limited to about 1:0.05 to about 1:5.

The sixth aspect of the present invention provides a process for the preparation of amorphous solid dispersion comprising of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1 and at least one pharmaceutically acceptable excipient, which comprising of:
  a) Dissolving a mixture of compound of formula-1 and at least one pharmaceutically acceptable excipient in a suitable solvent or mixture of solvents,
  b) removing the solvent(s) from the reaction mixture and drying the material to provide its corresponding amorphous solid dispersion.

Wherein,
in step-a) the suitable excipient is same as defined above in the second aspect;
  the suitable solvent can be selected from hydrocarbon solvents, ether solvents, ester solvents, polar-aprotic solvents, chloro solvents, ketone solvents, nitrile solvents, alcohol solvents, polar solvents, formic acid, acetic acid, alkyl ethers of ethylene glycol or propylene glycol or their mixtures; a mixture of compound of formula-1 and pharmaceutically acceptable excipient was dissolved in a suitable solvent by heating the mixture to a suitable temperature ranges from 0° C. to 150° C.;

After dissolving the mixture of compound of formula-1 and excipient in the solvent system, the solution may optionally be treated with charcoal or any other suitable material to remove color and/or to clarify the solution;

Optionally, the solution obtained above may be filtered to remove any insoluble particles. The solution may be filtered by passing through paper, glass fiber or other membrane material or a bed of a clarifying agent such as Celite® or hyflow. Depending upon the equipment used and the concentration and temperature of the solution, the filtration apparatus may need to be preheated to avoid premature crystallization.

In step-b) suitable techniques which may be used for the removal of solvent from the reaction mixture is same as defined above.

The preferred embodiment of the present invention provides a process for the preparation of amorphous solid dispersion comprising N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1 and at least one pharmaceutically acceptable excipient selected from PVP of different grades, HPC, HPMC, Eudragit L 100-55 and HPMCAS, which comprising of;
  a) Dissolving a mixture of compound of formula-1 and at least one pharmaceutically acceptable excipient selected from PVP of different grades, HPC, HPMC, Eudragit L 100-55 and HPMCAS in methanol,
  b) distilling off the solvent from the reaction mixture under reduced pressure and drying the material to provide its corresponding amorphous solid dispersion.

Figure 8:
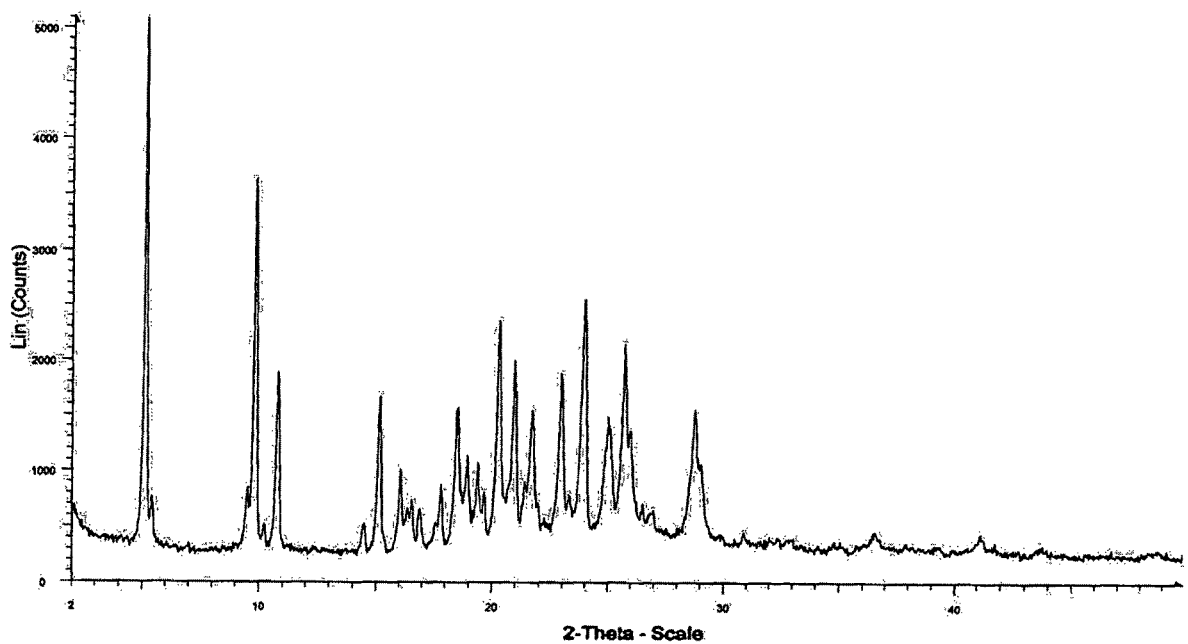
FIG. 8: Illustrates the powder X-ray diffraction pattern of crystalline form-M of compound of formula-1.

The seventh aspect of the present invention provides a novel crystalline form of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2), hereinafter designated as crystalline form-M. Further, the crystalline form-M is characterized by
  a) its powder X-ray diffraction pattern having peaks at 5.0, 9.4, 9.7, 10.7, 15.1, 16.0, 18.4, 18.8, 19.3, 20.2, 20.9, 21.6, 22.9, 23.9, 25.0, 25.7, 25.9, 28.7 and 29.0±0.2 degrees of 2-theta; and
  b) its powder X-ray diffraction pattern as illustrated in FIG. 8.

The eighth aspect of the present invention present invention provides a process for the preparation of crystalline form-M of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1, comprising of:
  a) Dissolving compound of formula-1 in dimethylformamide,
  b) adding ethylacetate to the solution obtained in step-(a),
  c) filtering the precipitated solid, washed with ethyl acetate and then dried to get crystalline form-M of compound of formula-1.

Figure 9:
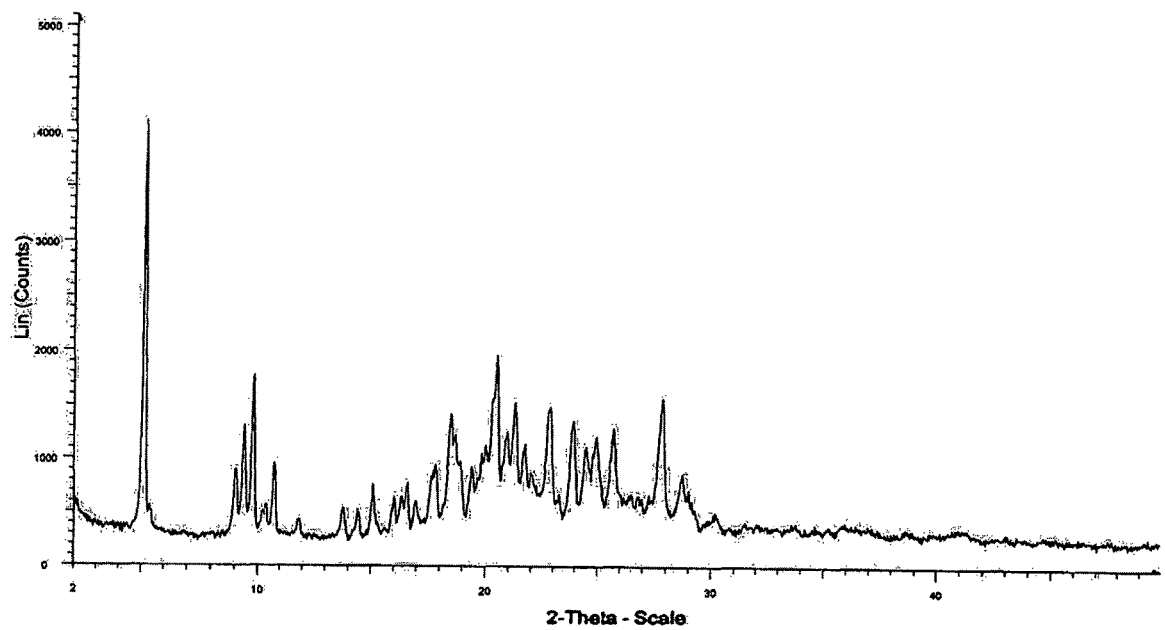
FIG. 9: Illustrates the powder X-ray diffraction pattern of crystalline form-S of compound of formula-1.

The ninth aspect of the present invention provides another novel crystalline form of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2), hereinafter designated as crystalline form-S. Further, the crystalline form-S is characterized by:
  a) its powder X-ray diffraction pattern having peaks at 5.0, 8.9, 9.3, 9.7, 10.6, 15.0, 17.7, 18.4, 18.8, 19.3, 19.9, 20.4, 20.8, 21.2, 21.6, 23.8, 24.4, 24.9, 25.6, 27.7 and 28.6±0.2 degrees of 2-theta; and
  b) its powder X-ray diffraction pattern as illustrated in FIG. 9.

The tenth aspect of the present invention present invention provides a process for the preparation of crystalline form-S of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1, comprising of:
  a) Dissolving compound of formula-1 in dimethylformamide,
  b) adding methyl tert-butyl ether to the solution obtained in step-(a),
  c) filtering the precipitated solid, washed with methyl tert-butyl ether and then dried to get crystalline form-S of compound of formula-1.

The eleventh aspect of the present invention provides an improved process for the preparation of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1, comprising of;
  a) Treating 7-flouro-6-nitroquinazolin-4(3H)-one compound of formula-2 with suitable chlorinating agent in presence of a suitable base in a suitable solvent to provide 4-chloro-7-fluoro-6-nitroquinazoline compound of formula-3,
  b) reacting compound of formula-3 in-situ with 3-chloro-4-fluoroaniline compound of formula-4 in presence of a suitable base in a suitable solvent to provide N-(3-chloro-4-fluorophenyl)-7-fluoro-6-nitroquinazolin-4-amine compound of formula-5, which is optionally purifying from a suitable solvent to provide pure N-(3-chloro-4-fluoro phenyl)-7-fluoro-6-nitroquinazolin-4-amine compound of formula-5,
  c) reacting compound of formula-5 with (S)-tetrahydrofuran-3-ol compound of formula-6 in presence of a suitable base in a suitable solvent to provide (S)—N-(3-chloro-4-fluorophenyl)-6-nitro-7-((tetrahydrofuran-3-yl)oxy)quinazolin-4-amine compound of formula-7,
  d) treating compound of formula-7 with a suitable reducing agent in a suitable solvent or mixture of solvents, which is optionally purifying from a suitable solvent to provide 4-[(3-Chloro-4-fluorophenyl)amino]-6-amino-7-((S)-tetrahydrofuran-3-yloxy)-quinazoline compound of formula-8, further treating the obtained compound with isopropyl alcohol in hydrochloric acid, which is optionally slurring in a suitable solvent to provide pure 4-[(3-Chloro-4-fluorophenyl)amino]-6-amino-7-((S)-tetrahydrofuran-3-yloxy)-quinazoline dihydrochloride compound of formula-8a,
  e) optionally, purifying the obtained compound of formula-8a with a suitable solvent or mixture of solvents to provide pure compound of formula-8a,
  f) converting (E)-4-(dimethylamino)but-2-enoic acid compound of formula-9 or its salts into its acid chloride by using a suitable chlorinating agent in a suitable solvent,
  g) reacting the compound of formula-8a obtained from step (d) or step-(e) with the acid chloride of compound of formula-9 obtained in step-(f) in presence of a suitable base in a suitable solvent to provide N-[4-[(3-chloro-4-fluorophenyl)amino]-7-[[(3S)-tetrahydro-3-furanyl]oxy]-6-quinazolinyl]-4-(dimethylamino)-(2E)-2-butenamide compound of formula-10, which is optionally purifying from a suitable solvent or mixture of solvents to provide pure N-[4-[(3-chloro-4-fluorophenyl)amino]-7-[[(3S)-tetrahydro-3-furanyl]oxy]-6-quinazolinyl]-4-(dimethylamino)-(2E)-2-butenamide compound of formula-10, h) treating compound of formula-10 with maleic acid in a suitable solvent to provide N-[[4-(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1.

Wherein in step-a) to step-h) the suitable solvent is selected from ester solvents, ether solvents, chloro solvents, hydrocarbon solvents, polar aprotic solvents, ketone solvents and alcohol solvents or mixture thereof, in step-a), b), c) & step-g) the suitable base is selected from organic base or inorganic base, in step-a) and step-f) the suitable chlorinating agent is selected from oxalyl chloride, thionyl chloride, phosphorous oxy chloride, phosphorous trichloride, phosphorous penta chloride and the like.

The preferred embodiment of the present invention provides a process for the preparation of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1, comprising of;

a) Treating 7-flouro-6-nitroquinazolin-4(3H)-one compound of formula-2 with phosphorous oxychloride in presence of triethylamine in acetonitrile provides 4-chloro-7-fluoro-6-nitroquinazoline compound of formula-3, b) reacting compound of formula-3 in-situ with 3-chloro-4-fluoroaniline compound of formula-4 in presence of potassium hydroxide in acetonitrile provides N-(3-chloro-4-fluorophenyl)-7-fluoro-6-nitroquinazolin-4-amine compound of formula-5, further purifying the obtained compound using 1,4-dioxane to provide pure N-(3-chloro-4-fluorophenyl)-7-fluoro-6-nitroquinazolin-4-amine compound of formula-5, c) reacting compound of formula-5 with (S)-tetrahydrofuran-3-ol compound of formula-6 in presence of potassium tert-butoxide in N-methyl-2-pyrrolidone provides (S)—N-(3-chloro-4-fluorophenyl)-6-nitro-7-((tetrahydrofuran-3-yl)oxy)quinazolin-4-amine compound of formula-7, d) treating compound of formula-7 with iron powder in presence of acetic acid in a mixture of tetrahydrofuran and water followed by purifying the obtained compound from ethyl acetate provides 4-[(3-Chloro-4-fluorophenyl) amino]-6-amino-7-((S)tetrahydrofuran-3-yloxy)-quinazoline compound of formula-8, which is further treating with isopropyl alcohol in hydrochloric acid provides pure 4-[(3-Chloro-4-fluorophenyl)amino]-6-amino-7-((S)tetrahydrofuran-3-yloxy)-quinazoline dihydrochloride compound of formula-8a, e) purifying the compound of formula-8a in a mixture of isopropanol and methanol provides pure compound of formula-8a, f) converting (E)-4-(dimethylamino)but-2-enoic acid hydrochloride compound of formula-9a into its acid chloride by using oxalyl chloride in acetonitrile and N,N-dimethylformamide, g) reacting the compound of formula-8a obtained from step-(d) or step-(e) with the acid chloride of compound of formula-9 obtained in step-(f) in presence of N-methyl-2-pyrrolidone in ethylacetate followed by purifying the obtained compound using isobutyl acetate and methyl cyclohexane provides 2-butenamide, N-[4-[(3-chloro-4-fluorophenyl)amino]-7-[[(3S)-tetrahydro-3-furanyl]oxy]-6-quinazolinyl]-4-(dimethylamino)-(2E)-2-butenamide compound of formula-10, h) treating compound of formula-10 with maleic acid in a mixture of isopropanol and isobutyl acetate provides N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1.

Figure 10:
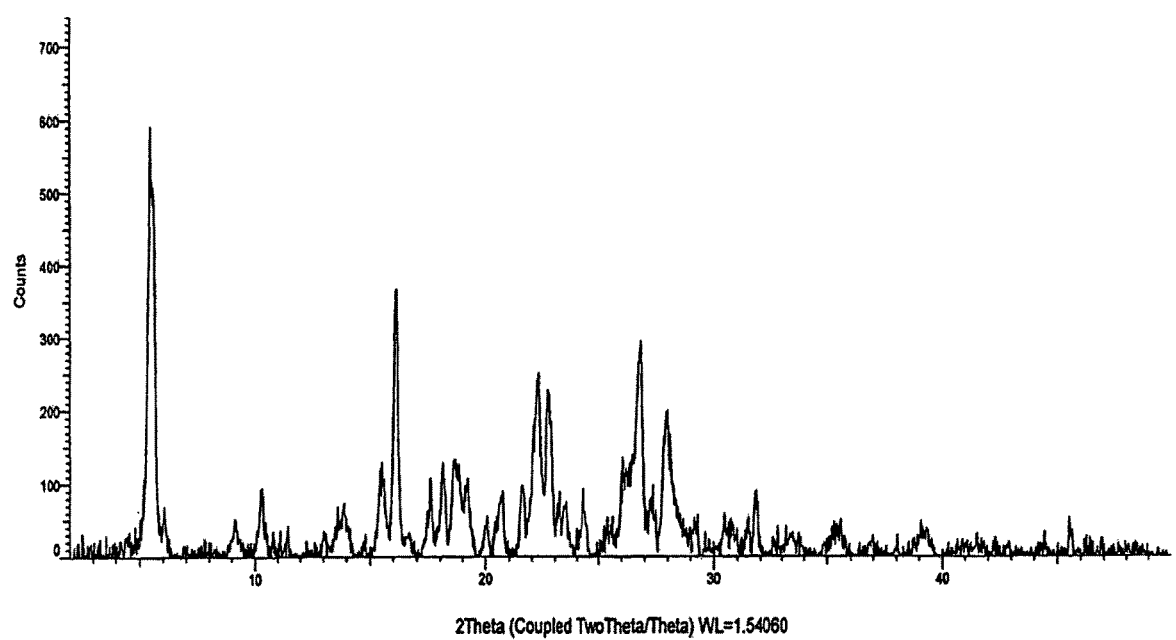

The twelfth aspect of the present invention provides a novel crystalline form of 4-[(3-chloro-4-fluorophenyl)amino]-6-amino-7-((S)-tetrahydrofuran-3-yloxy)-quinazoline dihydrochloride compound of formula-8a, hereinafter designated as crystalline form-M. The crystalline form-M is characterized by:

a) its powder X-ray diffraction pattern having peaks at 5.3, 5.7, 5.9, 9.0, 10.4, 11.5, 13.2, 13.4, 13.9, 15.3, 17.3, 18.6, 19.0, 19.4, 20.1, 20.6, 21.4, 22.1, 22.5, 24.1, 24.6, 25.9, 26.1, 26.6, 27.0, 28.5, 30.3, 31.2 and 33.2±0.2 degrees of 2-theta; and b) its powder X-ray diffraction pattern as shown in FIG. 10.

The thirteenth aspect of the present invention provides a process for the preparation of crystalline form-M of 4-[(3-Chloro-4-fluorophenyl)amino]-6-amino-7-((S)tetrahydrofuran-3-yloxy)-quinazoline dihydrochloride compound of formula-8a, comprising of;

a) Treating the (S)—N-(3-chloro-4-fluorophenyl)-6-nitro-7-((tetrahydrofuran-3-yl)oxy)quinazolin-4-amine compound of formula-7 with a suitable reducing agent, b) adding suitable solvent and stirring the reaction mixture, c) basifying the reaction mixture with a suitable aqueous base, d) filtering the reaction mixture, e) separating both the aqueous and organic layers, f) treating the organic layer with isopropanolic-HCl at a suitable temperature, g) filtering the precipitated solid provides crystalline form-M of 4-[(3-Chloro-4-fluorophenyl)amino]-6-amino-7-((S)tetrahydrofuran-3-yloxy)-quinazoline dihydrochloride compound of formula-8a.

Wherein in step-a), the suitable reducing agent is iron in presence of acetic acid; and in step-f) the suitable temperature is ranging from 0-5° C.

The preferred embodiment of the present invention provides a process for the preparation of crystalline form-M of 4-[(3-Chloro-4-fluorophenyl)amino]-6-amino-7-((S)-tetrahydrofuran-3-yloxy)-quinazoline dihydrochloride compound of formula-8a, comprising of;

a) Treating the (S)—N-(3-chloro-4-fluorophenyl)-6-nitro-7-((tetrahydrofuran-3-yl)oxy)quinazolin-4-amine compound of formula-7 with iron in presence of acetic acid, b) adding ethylacetate and stirring the reaction mixture, c) basifying the reaction mixture with aqueous sodium carbonate, d) filtering the reaction mixture, e) separating both the aqueous and organic layers, f) treating the organic layer with isopropanolic-HCl at 0-5° C., g) filtering the precipitated solid provides crystalline form-M of 4-[(3-Chloro-4-fluorophenyl)amino]-6-amino-7-((S)tetrahydrofuran-3-yloxy)-quinazoline dihydrochloride compound of formula-8a.

Figure 11:
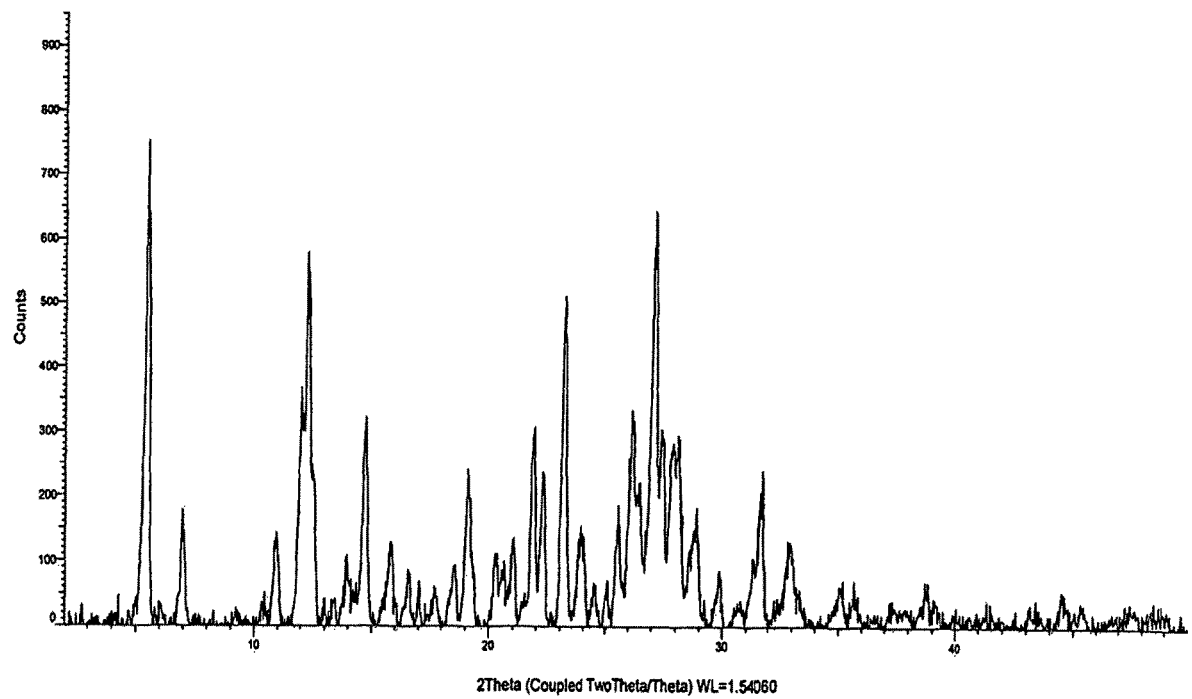

The fourteenth aspect of the present invention provides a novel crystalline form of 4-[(3-chloro-4-fluorophenyl)amino]-6-amino-7-((S)-tetrahydrofuran-3-yloxy)-quinazoline dihydrochloride compound of formula-8a, hereinafter designated as crystalline form-N. The crystalline form-N is characterized by:

a) its powder X-ray diffraction pattern having peaks at 5.4, 6.9, 9.2, 10.4, 10.9, 12.0, 13.9, 14.6, 15.7, 16.5, 18.4, 19.1, 20.3, 20.5, 20.9, 21.8, 22.2, 23.1, 23.8, 25.0, 25.5, 26.1, 26.3, 27.0, 27.3, 27.9, 28.7, 29.8, 31.3, 31.6, 32.8 and 35.0±0.2 degrees of 2-theta; and b) its powder X-ray diffraction pattern as shown in FIG. 11.

The fifteenth aspect of the present invention provides a process for the preparation of crystalline form-N of 4-[(3-Chloro-4-fluorophenyl)amino]-6-amino-7-((S)tetrahydrofuran-3-yloxy)-quinazoline dihydrochloride compound of formula-8a, comprising of;

a) Adding a suitable solvent or mixture of solvents to 4-[(3-chloro-4-fluorophenyl)amino]-6-amino-7-((S)-tetrahydrofuran-3-yloxy)-quinazoline dihydrochloride compound of formula-8a, b) stirring the reaction mixture at a suitable temperature, c) heating the reaction mixture at a suitable temperature, d) cooling the reaction mixture to a suitable temperature, e) filtering the solid, washing with a suitable solvent and then drying to get crystalline form-N of 4-[(3-Chloro-4-fluorophenyl)amino]-6-amino-7-((S)tetrahydrofuran-3-yloxy)-quinazoline dihydrochloride compound of formula-8a.

The preferred embodiment of the present invention provides a process for the preparation of crystalline form-N of 4-[(3-Chloro-4-fluorophenyl)amino]-6-amino-7-((S)tetrahydrofuran-3-yloxy)-quinazoline dihydrochloride compound of formula-8a, comprising of;

a) Adding a mixture of isopropanol and methanol to 4-[(3-chloro-4-fluorophenyl)amino]-6-amino-7-((S)-tetrahydrofuran-3-yloxy)-quinazoline dihydrochloride compound of formula-8a, b) stirring the reaction mixture at 25-30° C., c) heating the reaction mixture to 60-65° C., d) cooling the reaction mixture to 0-5° C., e) filtering the solid, washing with isopropanol and then drying to get crystalline form-N of 4-[(3-Chloro-4-fluorophenyl)amino]-6-amino-7-((S)tetrahydrofuran-3-yloxy)-quinazoline dihydrochloride compound of formula-8a.

The sixteenth aspect of the present invention provides process for the preparation of N-[4-[(3-chloro-4-fluorophenyl)amino]-7-[[(3S)-tetrahydro-3-furanyl]oxy]-6-quinazolinyl]-4-(dimethylamino)-(2E)-2-butenamide compound of formula-10, comprising of reacting the compound of formula-8 or its salts with the acid chloride of compound of formula-9 in presence of a suitable base in a suitable solvent, followed by optionally purifying the obtained compound from a suitable solvent or mixture of solvents to provide N-[4-[(3-chloro-4-fluorophenyl)amino]-7-[[(3S)-tetrahydro-3-furanyl]oxy]-6-quinazolinyl]-4-(dimethylamino)-(2E)-2-butenamide compound of formula-10.

Wherein the suitable solvent used is selected from ester solvents, ether solvents, chloro solvents, hydrocarbon solvents, ketone solvents and alcohol solvents or mixture thereof.

The preferred embodiment of the present invention provides a process for the preparation of N-[4-[(3-chloro-4-fluorophenyl)amino]-7-[[(3S)-tetrahydro-3-furanyl]oxy]-6-quinazolinyl]-4-(dimethylamino)-(2E)-2-butenamide compound of formula-10, comprising of reacting compound of formula-8a with the acid chloride of compound of formula-9 in presence of N-methyl-2-pyrrolidone in acetonitrile, followed by purifying the obtained compound using isobutyl acetate and methyl cyclohexane provides N-[4-[(3-chloro-4-fluoro phenyl)amino]-7-[[(3S)-tetrahydro-3-furanyl]oxy]-6-quinazolinyl]-4-(dimethylamino)-(2E)-2-butenamide compound of formula-10.

Figure 12:
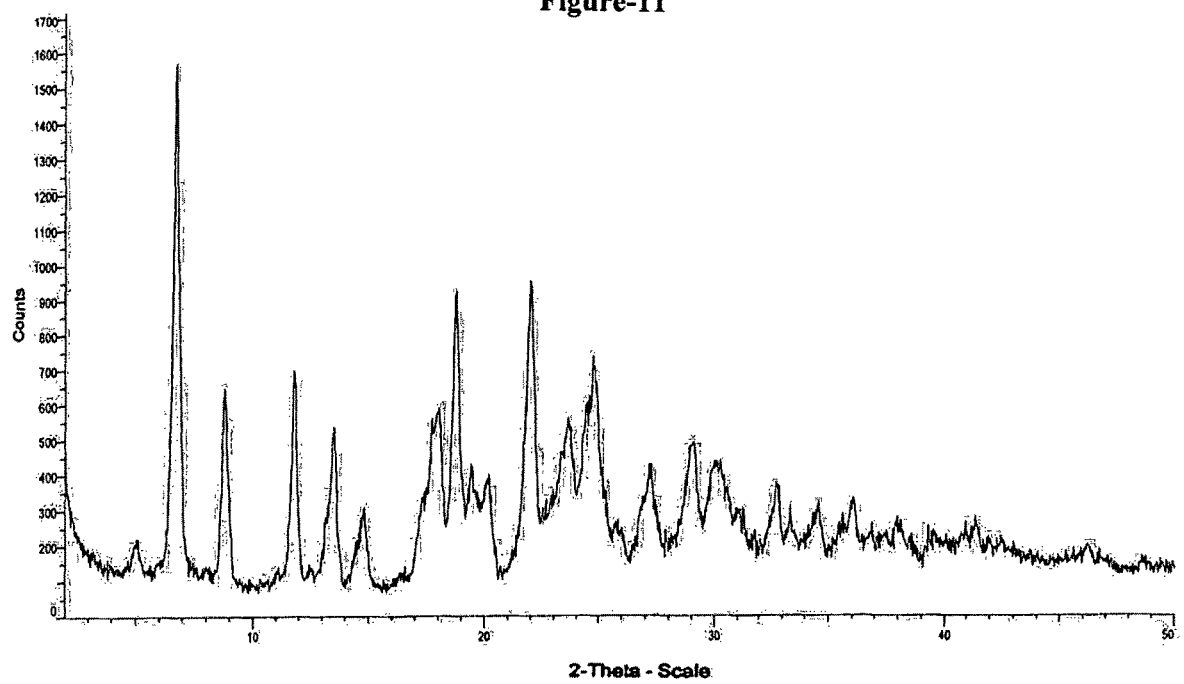
FIG. 12: Illustrates the PXRD pattern of novel crystalline Form-R of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1.

The seventeenth aspect of the present invention provides novel crystalline form of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1, hereinafter designated as crystalline form-R. The crystalline form-R is characterized by:

a) its powder X-ray diffraction pattern having peaks at 5.0, 6.7, 8.8, 11.7, 13.4, 14.7, 17.5, 17.9, 18.7, 19.4, 20.1, 21.9, 23.6, 24.5, 24.7, 25.8, 27.1, 29.0, 30.0, 30.9, 32.7, 33.3, 34.5, 36.0, 38.0 and 41.3±0.2 degrees of 2-theta; and b) its powder X-ray diffraction pattern as shown in FIG. 12.

The eighteenth aspect of the present invention provides a process for the preparation of novel crystalline form-R of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1, comprising of:

a) Adding a suitable solvent to the compound of formula-1, b) heating the reaction mixture to a suitable temperature, c) cooling the reaction mixture to a suitable temperature, d) filtering the solid and then drying to get crystalline form-R of 2-butenamide, N-[4-[(3-chloro-4-fluorophenyl)amino]-7-[[(3S)-tetrahydro-3-furanyl]oxy]-6-quinazolin yl]-4-(dimethylamino)-, (2E)-, (2Z)-2-butenedioate (1:2) compound of formula-1.

Wherein the suitable solvent used is selected from ester solvents, ether solvents, chloro solvents, hydrocarbon solvents, ketone solvents, polar aprotic solvents and alcohol solvents or mixture thereof.

The preferred embodiment of the present invention provides a process for the preparation of novel crystalline form-R of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1, comprising of;

a) Adding isobutyl acetate and nitromethane to compound of formula-1, b) heating the reaction mixture at 60° C. for 1 hr, c) cooling the reaction mixture to 40° C., d) filtering the solid and then drying to get crystalline form-R of N-[4-[(3-chloro-4-fluorophenyl)amino]-7-[[(3S)-tetrahydro-3-furanyl]oxy]-6-quinazolinyl]-4-(dimethyl amino)-, (2E)-, (2Z)-2-butenedioate (1:2) compound of formula-1.

The another embodiment of the present invention provides a process for the preparation of novel crystalline form-R of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1, comprising of:

a) Adding a suitable solvent to N-[4-[(3-chloro-4-fluorophenyl)amino]-7-[[(3S)-tetrahydro-3-furanyl]oxy]-6-quinazolinyl]-4-(dimethylamino)-(2E)-2-butenamide,
b) stirring the reaction mixture,
c) optionally, treating the reaction mixture with charcoal,
d) adding a suitable solvent to the maleic acid,
e) stirring the reaction mixture,
f) optionally, seeding the crystalline form-R of compound of formula-1 to the compound obtained in step-(e),
g) adding the reaction mixture obtained in step-b) or step-c) to the reaction mixture obtained in step-e) or step-f),
h) adding water to the reaction mixture obtained in step-g),
i) filtering the solid and then drying to get crystalline form-R of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1.

Wherein, the suitable solvent used in step-a) and d) is selected from ester solvents, ether solvents, chloro solvents, hydrocarbon solvents, ketone solvents, polar aprotic solvents and alcohol solvents or mixture thereof.

The preferred embodiment of the present invention provides a process for the preparation of novel crystalline form-R of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1, comprising of;
a) Adding a mixture of isopropanol and isobutyl acetate to N-[4-[(3-chloro-4-fluorophenyl)amino]-7-[[(3S)-tetrahydro-3-furanyl]oxy]-6-quinazolinyl]-4-(dimethylamino)-(2E)-2-butenamide,
b) stirring the reaction mixture,
c) treating the reaction mixture with charcoal,
d) adding a mixture of isopropanol and isobutyl acetate to maleic acid,
e) stirring the reaction mixture,
f) adding the reaction mixture obtained in step-c) to the reaction mixture obtained in step-c),
g) adding water to the reaction mixture,
h) filtering the solid and then drying to get crystalline form-R of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1.

The compound of formula-1 used herein the present invention can be prepared by the methods known in the art such as U.S. Pat. No. 8,426,586 B2, WO2013052157 A1 and IPCOM000240150D. And also compound of formula-1 can be prepared from the process disclosed in the present invention.

The amorphous, crystalline Form-M, Form-S and Form-R of compound of formula-1 can be useful for the preparation of pharmaceutical composition.

The crystalline Form-M and Form-N of compound of formula-8a are useful for the preparation of pure compound of formula-1.

The crystalline Form-R of compound of formula-1 obtained from the present invention is stable at various conditions and does not convert to any of the other crystalline forms.

P-XRD Method of Analysis:

PXRD analysis of the crystalline form-M of compound of formula-8a, crystalline form-R and amorphous compound of formula-1 of the present invention was carried out by using BRUKER/AXS X-Ray diffractometer using Cu Kα radiation of wavelength 1.5406 A° and at continuous scan speed of 0.03°/min.

The amorphous, crystalline Form-R, Form-M and Form-S. of Afatinib dimaleate of the present invention can be further micronized or milled by using conventional techniques to get the desired particle size to achieve desired solubility profile based on different forms of pharmaceutical composition requirements. Techniques that may be used for particle size reduction include, but not limited to ball, roller and hammer mills, and jet mills. Milling or micronization may be performed before drying, or after the completion of drying of the product.

The process of the present invention can be represented schematically as follows:

Scheme-I:

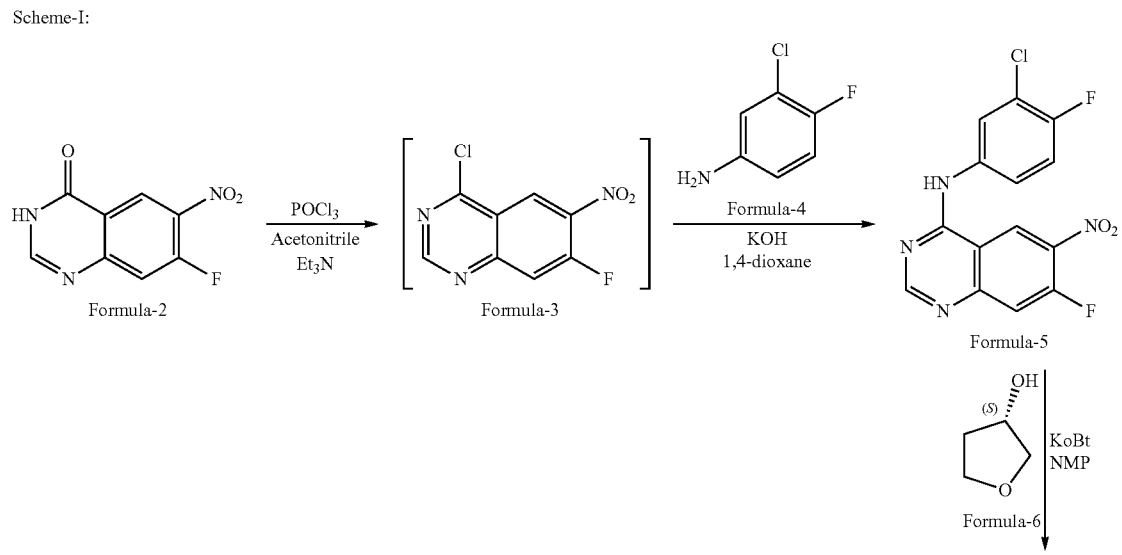

-continued

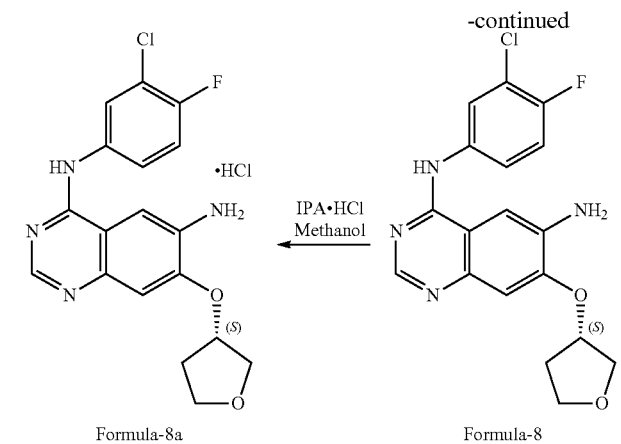
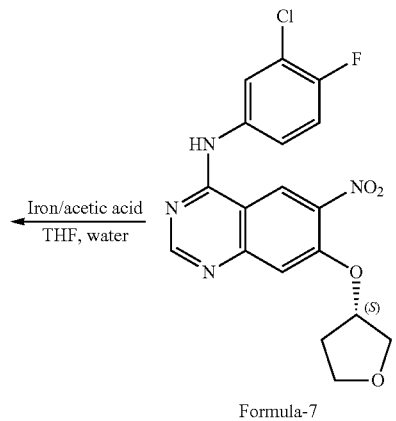
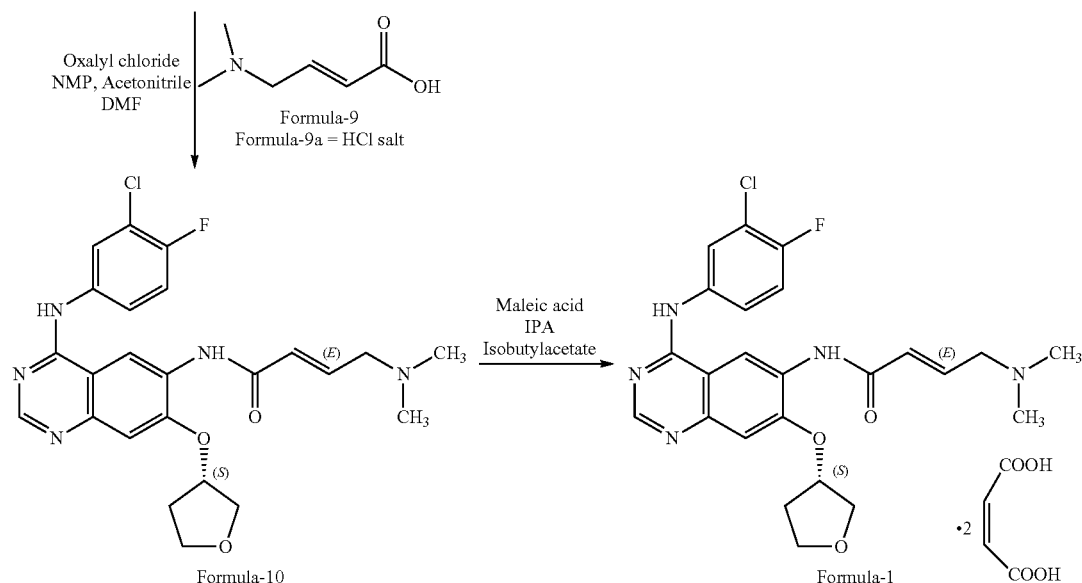

The best mode of carrying out the present invention is illustrated by the below mentioned examples. These examples are provided as illustration only and hence should not be construed as limitation of the scope of the invention.

EXAMPLES

Example-1: Preparation of Amorphous Afatinib Dimaleate 1 gm of Afatinib dimaleate was dissolved in 10 ml of water. The resulting clear solution was filtered through hyflow bed and frozen. The frozen mixture is lyophilized for 24 hrs to get amorphous Afatinib dimaleate.
Yield: 0.8 g.
The PXRD diffraction pattern of the obtained compound is shown in FIG. 1.

Example-2: Preparation of Amorphous Afatinib Dimaleate

Maleic acid (4.77 gms) was added to a mixture of Afatinib (10 gms) and water (100 ml) at 30-35° C. and stirred for 15 mins at 30-35° C. Filtered the reaction mixture through the hyflow bed and washed with water. The filtrate was frozen and lyophilized for 24 hrs to get the amorphous Afatinib dimaleate.

Yield: 8.5 gms
The powder X-ray diffraction pattern of the obtained compound is shown in FIG. 1.

Example-3: Preparation of pure amorphous N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) (Formula-1)

A mixture of compound of formula-1 (3.0 gms) and methanol (150 ml) was heated to 45-50° C. and stirred for 40 mins to get clear solution. Filtered the reaction mixture. Distilled off the solvent completely from the filtrate under reduced pressure and then dried the obtained compound to get title compound. Yield: 2.0 gms.
The powder X-ray diffraction pattern of the obtained compound is shown in FIG. 2.

Example-4: Preparation of Amorphous Solid Dispersion Comprising Compound of Formula-1 and Povidone k-30 (PVP K-30)

A mixture of compound of formula-1 (500 mg), PVP K-30 (500 mg) and methanol (20 ml) was heated to 45-50°

C. and stirred for 35 mins to get clear solution. Distilled off the solvent completely from the reaction mixture under reduced pressure and then dried the obtained material to get the title compound. Yield: 700.0 mg.

Figure 3:
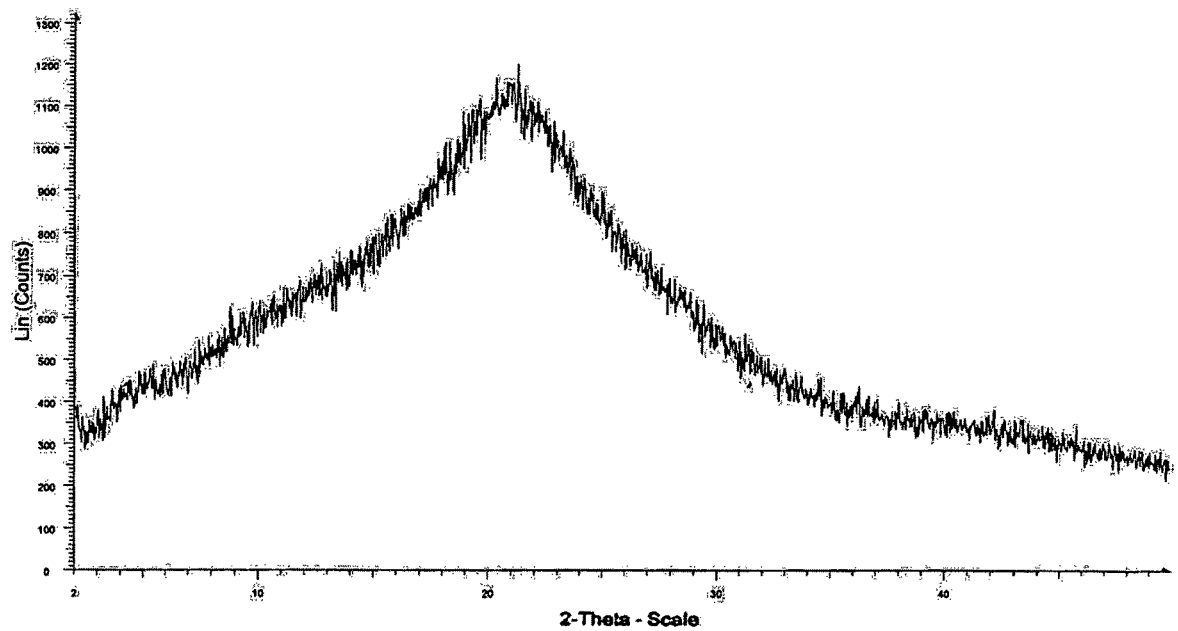
FIG. 3: Illustrates the powder X-ray diffraction pattern of amorphous solid dispersion comprising compound of formula-1 and PVP K-30.

The powder X-ray diffraction pattern of the obtained compound is shown in FIG. 3.

Example-5: Preparation of Amorphous Solid Dispersion Comprising Compound of Formula-1 and Hydroxypropyl Cellulose (HPC)

A mixture of compound of formula-1 (500 mg), hydroxypropyl cellulose (500 mg) and methanol (25 ml) was heated to 45-50° C. and stirred for 25 mins to get clear solution. Distilled off the solvent completely from the reaction mixture under reduced pressure and then dried the obtained material to get the title compound. Yield: 450.0 mg.

Figure 4:
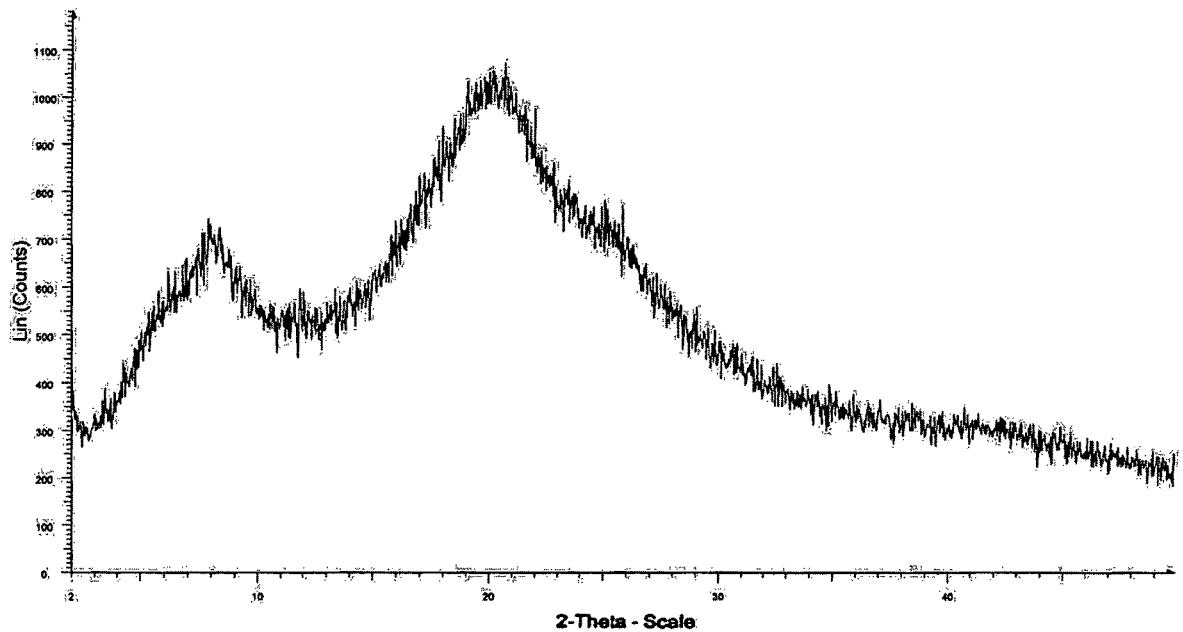
FIG. 4: Illustrates the powder X-ray diffraction pattern of amorphous solid dispersion comprising compound of formula-1 and hydroxypropyl cellulose (HPC).

The powder X-ray diffraction pattern of obtained compound is shown in FIG. 4.

Example-6: Preparation of Amorphous Solid Dispersion Comprising Compound of Formula-1 and Hydroxypropyl Methylcellulose (HPMC)

A mixture of compound of formula-1 (500 mg), hydroxypropyl methylcellulose (500 mg) and methanol (30 ml) was heated to 45-50 C and stirred for 25 mins to get clear solution. Distilled off the solvent completely from the reaction mixture under reduced pressure and then dried the obtained material to get the title compound. Yield: 700.0 mg.

Figure 5:
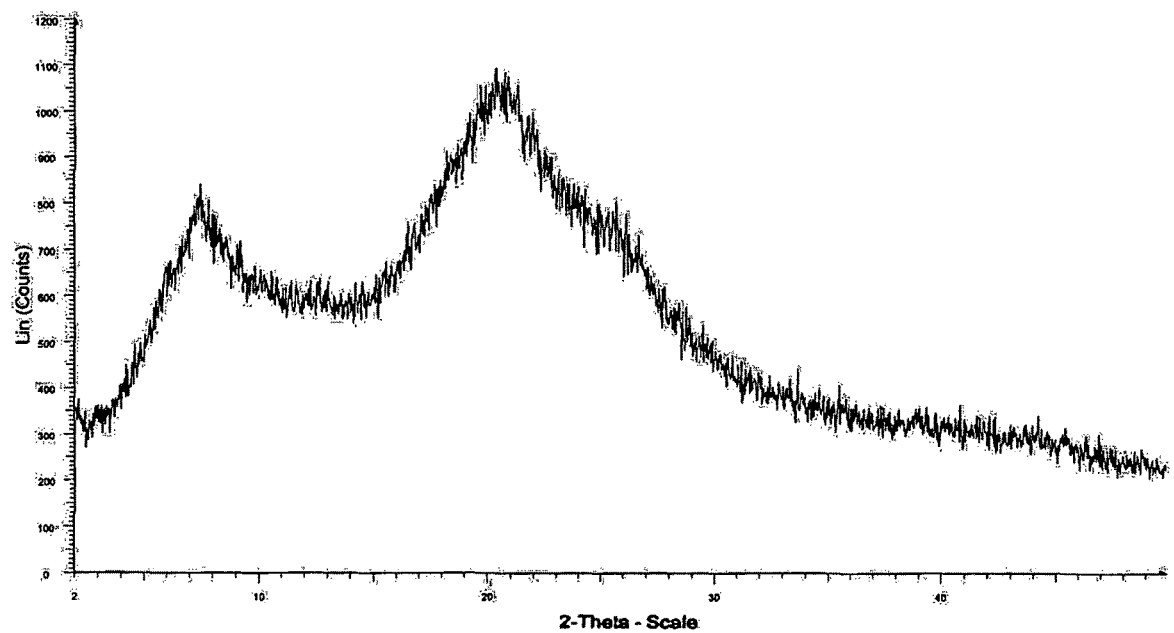
FIG. 5: Illustrates the powder X-ray diffraction pattern of amorphous solid dispersion comprising compound of formula-1 and hydroxypropyl methylcellulose (HPMC).

The powder X-ray diffraction pattern of the obtained compound is shown in FIG. 5.

Example-7: Preparation of Amorphous Solid Dispersion Comprising Compound of Formula-1 and Eudragit L 100-55

A mixture of compound of formula-1 (500 mg), Eudragit L 100-55 (500 mg) and methanol (40 ml) was heated to 45-50° C. and stirred for 30 mins to get clear solution. Distilled off the solvent completely from the reaction mixture under reduced pressure and then dried the obtained material to get the title compound. Yield: 600.0 mg.

Figure 6:
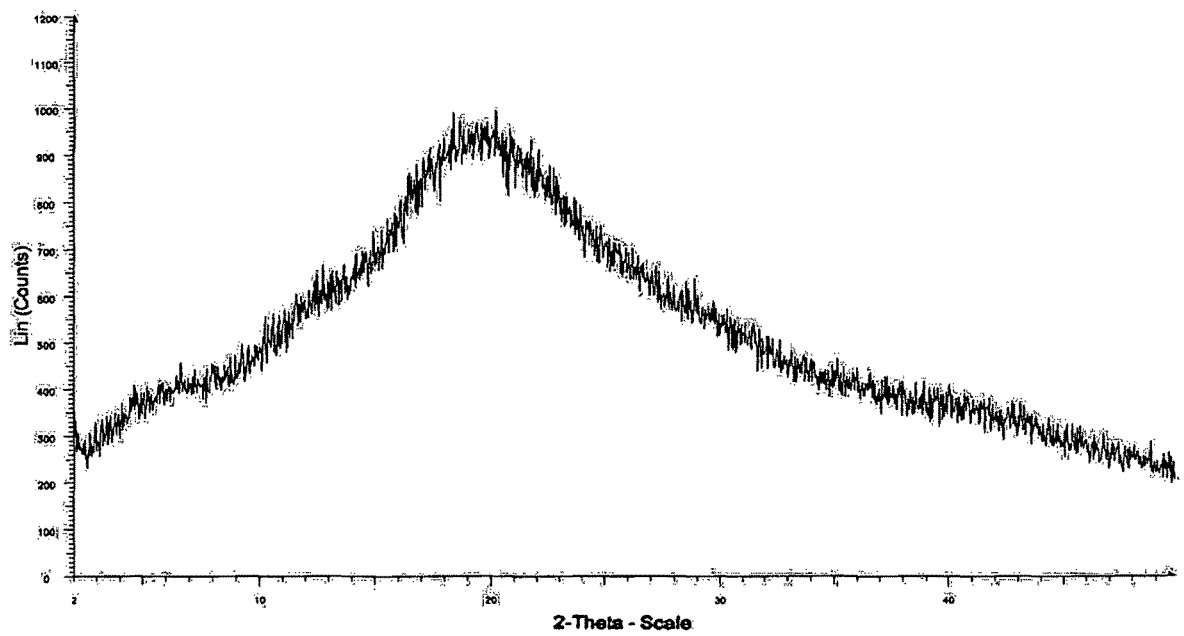
FIG. 6: Illustrates the powder X-ray diffraction pattern of amorphous solid dispersion comprising compound of formula-1 and Eudragit L 100-55.

The powder X-ray diffraction pattern of obtained compound is shown in FIG. 6.

Example-8: Preparation of Amorphous Solid Dispersion Comprising Compound of Formula-1 and Hydroxypropyl Methylcellulose Acetate Succinate (HPMCAS)

A mixture of compound of formula-1 (500 mg), HPMCAS (500 mg) and methanol (40 ml) was heated to 45-50° C. and stirred for 25 mins to get clear solution. Distilled off the solvent completely from the reaction mixture under reduced pressure and then dried the obtained material to get the title compound. Yield: 550.0 mg.

Figure 7:
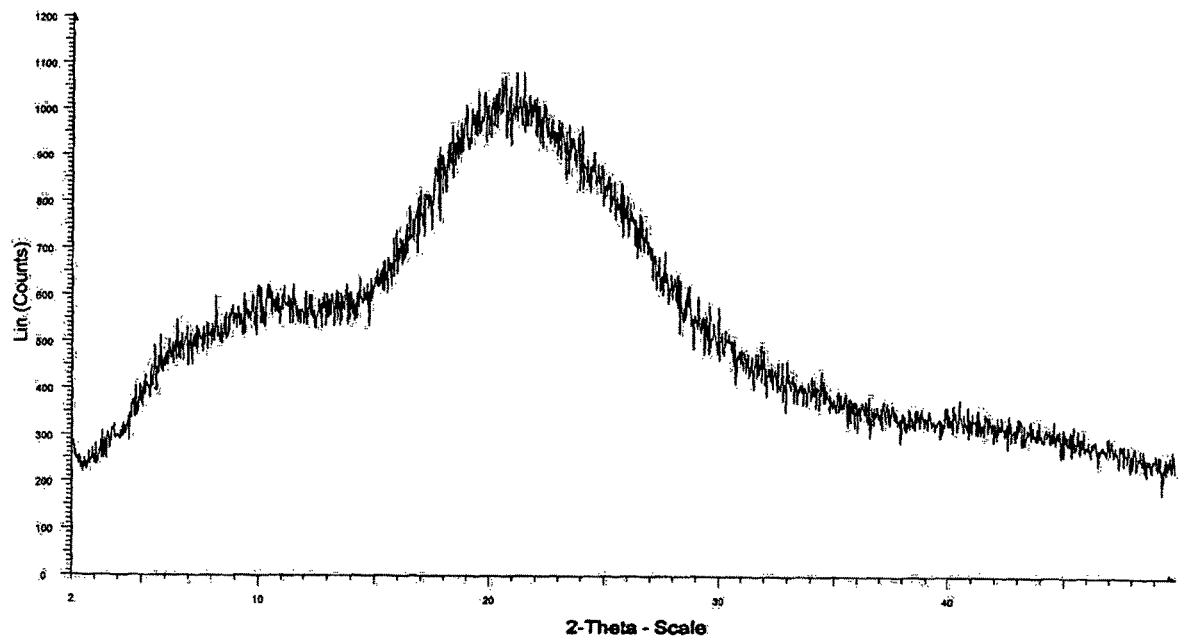
FIG. 7: Illustrates the powder X-ray diffraction pattern of amorphous solid dispersion comprising compound of formula-1 and hydroxypropyl methylcellulose acetate succinate (HPMCAS).

The powder X-ray diffraction pattern of obtained compound is shown in FIG. 7.

Example-9: Preparation of Crystalline Form-M of Compound of Formula-1

A mixture of compound of formula-1 (2 gms) and dimethylformamide (12 ml) was stirred for 15 min at 25-30° C. to get clear solution. Ethyl acetate (30 ml) was added to the above solution at 25-30° C. and stirred for 1 hr 30 mins. Filtered the precipitated solid, washed with ethyl acetate and then dried to get title compound. Yield: 1.2 gms.

The powder X-ray diffraction pattern of the obtained compound is shown in FIG. 8.

Example-10: Preparation of Crystalline Form-S of Compound of Formula-1

A mixture of compound of formula-1 (2 gms) and dimethylformamide (12 ml) was stirred for 15 min at 25-30° C. to get clear solution. Methyl tert-butyl ether (30 ml) was added to the above solution at 25-30° C. and stirred for 1 hr 50 mins. Filtered the precipitated solid, washed with methyl tert-butyl ether and then dried to get title compound. Yield: 1.8 gms.

The powder X-ray diffraction pattern of the obtained compound is shown in FIG. 9.

Example-11: Preparation of N-(3-chloro-4-fluorophenyl)-7-fluoro-6-nitroquinazolin-4-amine (Formula-5)

Phosphorous oxychloride (146.8 gm) was added to a mixture of 7-flouro-6-nitroquinazolin-4(3H)-one compound of formula-2 (100 gm) and acetonitrile (400 ml) at 25-30° C. Cooled the reaction mixture to 0-5° C. Triethylamine (58 gm) was slowly added to the reaction mixture at 0-5° C. Heated the reaction mixture to 80-85° C. and stirred for 5 hrs at the same temperature. Cooled the reaction mixture to 25-30° C. A solution of 3-chloro-4-flouro aniline compound of formula-4 (83.5 gm) in acetonitrile (200 ml) was added to the reaction, mixture at 25-30° C. and stirred for 3 hrs at the same temperature. Water was added to the reaction mixture at 25-30° C. Basified the reaction mixture using aqueous potassium hydroxide solution and stirred for 60 minutes at 25-30° C. The solid formed was filtered, washed with water and dried to get the title compound.

Example-12: Purification of N-(3-chloro-4-fluorophenyl)-7-fluoro-6-nitroquinazolin-4-amine (Formula-5)

1,4-Dioxane (500 ml) was added to the compound obtained in example-11. Heated the reaction mixture to 70-75° C. and stirred for 30 minutes at the same temperature. Cooled the reaction mixture to 25-30° C. and stirred for 20 minutes at the same temperature. The solid formed was filtered, washed with dioxane and dried to get the title compound.

Yield: 153 g; MR: 225-235° C.; Purity: 99.6% by HPLC

Example-13: Preparation of (S)—N-(3-chloro-4-fluorophenyl)-6-nitro-7-(tetrahydrofuran-3-yloxy) quinazolin-4-amine (Formula-7)

A mixture of N-(3-chloro-4-fluorophenyl)-7-fluoro-6-nitroquinazolin-4-amine compound of formula-5 (100 gm), (S)-tetrahydrofuran-3-ol compound of formula-6 (31.4 gm) and N,N-dimethyl formamide (500 ml) was stirred at 25-30° C. for 10 minutes under nitrogen atmosphere. Cooled the reaction mixture to 15-20° C. Potassium tertiarybutoxide (66.6 gm) was added to the reaction mixture at 15-20° C. and stirred for 90 minutes at the same temperature. Cooled the reaction mixture to 10-15° C. Water (1600 ml) was slowly added to the reaction mixture at below 20° C. Stirred for 3 hrs at 25-30° C. The solid formed was filtered, washed with water and dried to get the title compound.

Yield: 114.2 g; MR: 225-235° C.

Example-14: Preparation of 4-[(3-Chloro-4-fluorophenyl)amino]-6-amino-7-((S)-tetrahydrofuran-3-yloxy)-quinazoline dihydrochloride (Formula-8a)

Acetic acid (81.5 gm) was added to a mixture of (S)—N-(3-chloro-4-fluorophenyl)-6-nitro-7-((tetrahydrofuran-3-yl)oxy)quinazolin-4-amine compound of formula-7 (100 gm), tetrahydrofuran (800 ml) and water (4000 ml) at 25-30° C. Iron (49.1 gm) was added to slowly to the reaction mixture at 25-30° C. and stirred for 3 hrs at the same temperature. Filtered the reaction mixture and washed with tetrahydrofuran. Water was added to the filtrate at 25-30° C. Basified the reaction mixture with aqueous sodium carbonate solution at, 25-30° C. and stirred for 3 hrs at the same temperature. The solid formed was filtered, washed with water and dried. Ethyl acetate (800 ml) was added to the obtained compound. Heated the reaction mixture to reflux for 30 minutes. Filtered the reaction mixture and washed with ethyl acetate. The filtrate was cooled to 25-30° C. Isopropanolic HCl (120.5 ml) was slowly added to the filtrate at 25-30° C. and stirred for 90 minutes at the same temperature. The solid formed was filtered and washed with ethyl acetate and dried to get the title compound.

Yield: 65 g; MR: 275-280° C.

Example-15: Purification of 4-[(3-Chloro-4-fluorophenyl)amino]-6-amino-7-((S)-tetrahydrofuran-3-yloxy)-quinazoline dihydrochloride (Formula-8a)

Methanol (225 ml) was added to the compound obtained in example-14. Heated the reaction mixture to 60-65° C. and stirred for 30 minutes at the same temperature. Cooled the reaction mixture to 0-5° C. and stirred for 90 minutes at the same temperature. The solid formed was filtered, washed with methanol and dried to get the title compound.

Yield: 60 g; MR: 275-280° C.; The PXRD of the obtained compound is shown in FIG. 1.

Example-16: Preparation of 4-[(3-Chloro-4-fluorophenyl)amino]-6-amino-7-((S)tetrahydrofuran-3-yloxy)-quinazoline (Formula-8)

Acetic acid (81.5 gm) was added to a mixture of (S)—N-(3-chloro-4-fluorophenyl)-6-nitro-7-((tetrahydrofuran-3-yl)oxy)quinazolin-4-amine compound of formula-7 (100 gm), tetrahydrofuran (800 ml) and water (4000 ml) at 25-30° C. Iron (49.1 gm) was added to slowly to the reaction mixture at 25-30° C. and stirred for 3 hrs at the same temperature. Filtered the reaction mixture and washed with tetrahydrofuran. Water was added to the filtrate at 25-30° C. Basified the reaction mixture with aqueous sodium carbonate solution at 25-30° C. and stirred for 3 hrs at the same temperature. The solid formed was filtered, washed with water and dried to get the title compound. Yield: 54 g.

Example-17: Purification of 4-[(3-Chloro-4-fluorophenyl)amino]-6-amino-7-((S)-tetrahydrofuran-3-yloxy)-quinazoline dihydrochloride (Formula-8a)

The 4-[(3-Chloro-4-fluorophenyl)amino]-6-amino-7-((S)tetrahydrofuran-3-yloxy)-quinazoline compound of formula-8 obtained from example-16 was cooled to 25-30° C. Isopropanolic HCl (120.5 ml) was slowly added to the reaction mixture at 25-30° C. and stirred for 90 minutes at the same temperature. The solid formed was filtered and washed with ethyl acetate and dried to get the title compound. Yield: 62 g; MR: 275-280° C.

Example-18: Preparation of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (Formula-10)

Step a):
(E)-4-(dimethylamino)but-2-enoic acid hydrochloride compound of formula-9a (40.2 gm), acetonitrile (580 ml) and N,N-dimethylformamide (3 ml) was stirred at 25-30° C. for 15 minutes under nitrogen atmosphere. Thionyl chloride (34.6 gm) was slowly added to the reaction at 25-30° C. and stirred the reaction mixture for 3 hrs at the same temperature. The obtained acid chloride is directly used for the further reaction.

Step b):
A mixture of 4-[(3-Chloro-4-fluorophenyl)amino]-6-amino-7-((S)-tetrahydrofuran-3-yloxy)-quinazoline dihydrochloride compound of formula-8a (50 gm) and ethyl acetate HCl (267 ml) was stirred at 25-30° C. Heated the reaction mixture at 60-65° C. and stirred for 15 minutes at the same temperature. Distilled off the solvent completely from the reaction mixture. N-methyl-2-pyrrolidone (500 ml) was added to the reaction mixture at 55-60° C. and stirred for 15 minutes at the same temperature. The acid chloride compound obtained in step a) was slowly added to the reaction mixture at 55-60° C. and stirred for 3 hrs at the same temperature. Cooled the reaction mixture to 25-30° C. Water (100 ml) was added to the reaction mixture at 25-30° C. and stirred for 15 minutes at the same temperature. Adjusted the pH of the reaction mixture to 4-5 by using aqueous sodium carbonate solution. Ethyl acetate (100 ml) was added to the reaction mixture at 25-30° C. and stirred for 15 minutes at the same temperature. Both the organic and aqueous layers were separated. The aqueous layer was basified with aqueous sodium carbonate solution and stirred for 15 minutes. Ethyl acetate (500 ml) was added to the reaction mixture and stirred for 10 minutes. Both the organic and aqueous layers were separated. The aqueous layer was extracted with ethyl acetate. Combined the organic layers and distilled off the solvent completely from the organic layer. Water (400 ml) was added to the obtained compound at 25-30° C. and stirred for 3 hrs at the same temperature. The solid was filtered, washed with water and dried. Isobutyl acetate (250 ml) was added to the obtained compound. Heated the reaction mixture to 85-90° C. Methyl cyclohexane (250 ml) was added slowly to the reaction mixture at 85-90° C. The reaction mixture was filtered through hyflow bed and washed with isobutyl acetate. Cooled the filtrate to 25-30° C. and stirred for 90 minutes at the same temperature. The solid formed was filtered and washed with methyl cyclohexane. The Iso butyl acetate (200 ml) was added to the obtained compound. Heated the reaction mixture to 85-90° C. Methyl cyclohexane (200 ml) was slowly added to the reaction mixture at 85-90° C. Cooled the reaction mixture to 25-30° C. and stirred for 90 minutes at the same temperature. The solid formed was filtered, washed with methyl cyclohexane and dried to get the title compound.

Yield: 35 g; MR: 135-145° C.

Example-19: Preparation of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (Formula-10)

(E)-4-(dimethylamino)but-2-enoic acid hydrochloride compound of formula-9a (20.1 gm), acetonitrile (290 ml)

and N,N-dimethylformamide (1.5 ml) was stirred at 25-30° C. for 15 minutes under nitrogen atmosphere. Thionyl chloride (17.3 gm) was slowly added to the reaction at 25-30° C. and stirred the reaction mixture for 3 hrs at the same temperature. The obtained acid chloride was slowly added to a reaction mixture of 4-[(3-Chloro-4-fluorophenyl) amino]-6-amino-7-((S)tetrahydrofuran-3-yloxy)-quinazoline dihydro chloride compound of formula-8a (25 gm) in N-methyl-2-pyrrolidone (250 ml) at 55-60° C. Stirred the reaction mixture for 3 hrs at the same temperature. Cooled the reaction mixture to 25-30° C. Water (50 ml) was added to the reaction mixture at 25-30° C. and stirred for 15 minutes at the same temperature. Adjusted the pH of the reaction mixture to 4-5 by using aqueous sodium carbonate solution. Ethyl acetate (50 ml) was added to the reaction mixture at 25-30° C. and stirred for 15 minutes at the same temperature. Both the organic and aqueous layers were separated. The aqueous layer was basified with aqueous sodium carbonate solution and stirred for 15 minutes. Ethyl acetate (250 ml) was added to the reaction mixture and stirred for 10 minutes. Both the organic and aqueous layers were separated. The aqueous layer was extracted with ethyl acetate. Combined the organic layers and distilled off the solvent completely from the organic layer. Water (200 ml) was added to the obtained compound at 25-30° C. and stirred for 3 hrs at the same temperature. The solid was filtered, washed with water and dried. Isobutyl acetate (125 ml) was added to the obtained compound. Heated the reaction mixture to 85-90° C. Methyl cyclohexane (125 ml) was added slowly to the reaction mixture at 85-90° C. The reaction mixture was filtered through hyflow bed and washed with isobutyl acetate. Cooled the filtrate to 25-30° C. and stirred for 90 minutes at the same temperature. The solid formed was filtered and washed with methyl cyclohexane. The Iso butyl acetate (100 ml) was added to the obtained compound. Heated the reaction mixture to 85-90° C. Methyl cyclohexane (100 ml) was slowly added to the reaction mixture at 85-90° C. Cooled the reaction mixture to 25-30° C. and stirred for 90 minutes at the same temperature. The solid formed was filtered, washed with methyl cyclohexane and dried to get the title compound. Yield: 17 g; MR: 136-144° C.

Example-20: Preparation of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (2Z)-2-butenedioate (1:2) (Formula-1)

A mixture of N-[4-[(3-chloro-4-fluorophenyl)amino]-7-[[(3S)-tetrahydro-3-furanyl]oxy]-6-quinazolinyl]-4-(dimethylamino)-(2E)-2-butenamide compound of formula-10 (25 gm) and ethanol (175 ml) was stirred for 15 minutes under nitrogen atmosphere. Cooled the reaction mixture to 0-5° C. 12.62 gm of Maleic acid in 75 ml ethanol was slowly added to the reaction mixture at 0-5° C. and stirred for 3 hrs at the same temperature. The solid formed was filtered under nitrogen atmosphere, washed with ethanol and dried to get the title compound.
Yield: 27 g; MR: 172-178° C.

Example-21: Preparation of crystalline form-R of N-[4-[(3-chloro-4-fluorophenyl) amino]-7-[[(3S)-tetrahydro-3-furanyl]oxy]-6-quinazolinyl]-4-(dimethylamino)-(2E)-2-butenamide (2Z)-2-butenedioate (1:2) compound of formula-1 (Formula-1)

Isobutyl acetate (25 ml) and nitromethane (25 ml) were added to N-[4-[(3-chloro-4-fluorophenyl)amino]-7-[[(3 S)-tetrahydro-3-furanyl]oxy]-6-quinazolinyl]-4-(dimethylamino)-(2E)-2-butenamide (2Z)-2-butenedioate (1:2) compound of formula-1 (5 gm). Heated the reaction mixture to 60° C. and stirred for 1 hr at the same temperature. Cooled the reaction mixture to 40° C. and stirred for 30 minutes at the same temperature. Further heated the reaction mixture to 60° C. and stirred for 1 hr at the same temperature and then cooled to 40° C. This process of heating and cooling is repeated for 5 times. The solid formed was filtered at 40° C. and dried to get the title compound. Yield: 4 gms;
The PXRD of the obtained compound is shown in FIG. 12.

Example-22: Preparation of (S)—N-(3-chloro-4-fluorophenyl)-6-nitro-7-(tetrahydrofuran-3-yloxy) quinazolin-4-amine (Formula-7)

A mixture of N-(3-chloro-4-fluorophenyl)-7-fluoro-6-nitroquinazolin-4-amine compound of formula-5 (100 gm), (S)-tetrahydrofuran-3-ol compound of formula-6 (31.4 gm) and N-methylpyrrolidone (300 ml) was stirred at 25-30° C. for 10 minutes under nitrogen atmosphere. Cooled the reaction mixture to 15-20° C. Potassium tertiarybutoxide (73.3 gm) was added to the reaction mixture at 15-20° C. and stirred for 90 minutes at the same temperature. Water (2000 ml) was slowly added to the reaction mixture at 15-20° C. Stirred it for 3 hrs at 25-30° C. The precipitated solid was filtered, washed with water and dried to get the title compound.
Yield: 114.2 g.

Example-23: Purification of (S)—N-(3-chloro-4-fluorophenyl)-6-nitro-7-(tetrahydrofuran-3-yloxy) quinazolin-4-amine (Formula-7)

Acetonitrile (500 ml) was added to the compound obtained in example-22 and stirred at 25-30° C. for 10 minutes. Heated the reaction mixture to 70-75° C. and stirred for 45 minutes at the same temperature. Cooled the reaction mixture to 25-30° C. and stirred for 90 minutes at the same temperature. The precipitated solid was filtered, washed with acetonitrile and dried to get the title compound.
Yield: 115.50 g; MR: 245-246° C.

Example-24: Preparation of 4-[(3-Chloro-4-fluorophenyl)amino]-6-amino-7-((S)tetrahydrofuran-3-yloxy)-quinazoline dihydrochloride (Formula-8a)

Acetic acid (81.5 gm) was added to a mixture of (S)—N-(3-chloro-4-fluorophenyl)-6-nitro-7-((tetrahydrofuran-3-yl)oxy)quinazolin-4-amine compound of formula-7 (100 gm), tetrahydrofuran (400 ml) and water (400 ml) at 25-30° C. Iron (49.1 gm) was slowly added to the reaction mixture at 25-30° C. and stirred for 3 hrs at the same temperature. Ethylacetate (200 ml) was added to the reaction mixture at 25-30° C. and stirred for 30 minutes at the same temperature. Basified the reaction mixture using aqueous sodium carbonate solution at 25-30° C. and stirred for 90 minutes at the same temperature. Filtered the unwanted solid through hyflow bed and washed the bed with pre-heated ethylacetate. Both the organic and aqueous layers were separated. Extracted the aqueous layer with ethylacetate. Combined the organic layers and washed with aqueous sodium chloride solution. The organic layer was cooled to 0-5° C. Isopropanalic-HCl (IPA-HCl) (193.2 ml) was slowly added to the reaction mixture at 0-5° C. and stirred for 90 minutes. The precipitated solid was filtered, washed with ethyl acetate and dried to get the title compound.

Yield: 90 g; MR: 266-270° C. Purity: 97.81% by HPLC.

The PXRD of the obtained compound is shown in FIG. 10.

Example-25: Purification of 4-[(3-Chloro-4-fluorophenyl)amino]-6-amino-7-((S)tetrahydrofuran-3-yloxy)-quinazoline dihydrochloride (Formula-8a)

Isopropanol (500 ml) and methanol (250 ml) was added to the 4-[(3-Chloro-4-fluorophenyl)amino]-6-amino-7-((S)tetrahydrofuran-3-yloxy)-quinazoline dihydrochloride compound of formula-8a at 25-30° C. and stirred for 10 minutes. Healted the reaction mixture to 60-65° C. and stirred for 45 minutes at the same temperature. Cooled the reaction mixture to 25-30° C. and further cooled to 0-5° C. Stirred the reaction mixture for 90 minutes at 0-5° C. The solid formed was filtered, washed with isopropanol and dried to get the title compound.

Yield: 85 g; MR: 266-270° C. Purity: 99.12% by HPLC.

The PXRD of the obtained compound is shown in FIG. 11.

Example-26: Preparation of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (Formula-10)

Step a):

(E)-4-(dimethylamino)but-2-enoic acid hydrochloride compound of formula-9a (64.4 gm), acetonitrile (500 ml) and N,N-dimethylformamide (5 ml) was stirred at 25-30° C. for 15 minutes under nitrogen atmosphere. Cooled the reaction mixture to 15-20° C. for 15 minutes under nitrogen atmosphere. Oxalyl chloride (43.19 gm) was slowly added to the reaction mixture at 15-20° C. and stirred the reaction mixture for 2 hrs at the same temperature. The obtained acid chloride is directly used for the further reaction.

Step b):

A mixture of 4-[(3-Chloro-4-fluorophenyl)amino]-6-amino-7-((S)-tetrahydro furan-3-yloxy)-quinazoline dihydrochloride compound of formula-8a (100 gm) and N-methyl-2-pyrrolidone (500 ml) was stirred at 25-30° C. Cooled the reaction mixture to 0-5° C. for 15 minutes under nitrogen atmosphere. The acid chloride compound obtained in step a) was slowly added to the reaction mixture at 0-5° C. and stirred for 2 hrs at the same temperature. Pre-cooled ethylacetate and pre-cooled water were slowly added to the reaction mixture at 0-5° C. and stirred for 15 at the same temperature. Basified the reaction mixture using aqueous sodium carbonate solution. Both the organic and aqueous layers were separated. The aqueous layer was extracted with ethyl acetate. Combined the organic layers and distilled off the solvent completely from the organic layer. Water (1000 ml) was added to the obtained compound at 25-30° C. and stirred for 5 hrs at the same temperature. The solid was filtered, washed with water and dried.

Example-27: Purification of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (Formula-10)

Step-(a):

N-methyl-2-pyrrolidone (200 ml) was added to the compound obtained in example-26 and stirred at 25-30° C. for 15 minutes. Water (400 ml) was added to the reaction mixture and stirred at 25-30° C. for 2 hrs. Filtered the precipitated solid and repeated the process again to get the title compound.

Yield: 90 g;

Step-(b):

Isobutyl acetate (700 ml) was added to the compound obtained in step-(a). Heated the reaction mixture to 80-85° C. and stirred for 30 minutes at the same temperature. Cooled the reaction mixture to 25-30° C. and stirred for 60 minutes at the same temperature. The solid formed was filtered, washed with isobutyl acetate and dried to get the title compound.

Yield: 75 g; Purity: 99.8% by HPLC; MR: 90-95° C.

Example-28: Purification of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (Formula-10)

Step-(a):

N-methyl-2-pyrrolidone (200 ml) was added to the compound obtained in example-26 and stirred at 25-30° C. for 15 minutes. Water (400 ml) was added to the reaction mixture and stirred at 25-30° C. for 2 hrs. Filtered the precipitated solid and repeated the process again to get the title compound.

Yield: 90 g.

Step-(b):

n-butyl acetate (500 ml) was added to the compound obtained in step-(a) and stirred for 15 minutes at the same temperature. Heated the reaction mixture to 80-85° C. Methyl cyclohexane (500 ml) was slowly added to the reaction mixture at 80-85° C. and stirred for 30 minutes at the same temperature. Cooled the reaction mixture to 25-30° C. and stirred for 60 minutes at the same temperature. The solid formed was filtered, washed with n-butyl acetate and dried to get the title compound.

Yield: 75 g; Purity: 99.8% by HPLC; MR: 90-95° C.

Example-29: Purification of N-[4-[(3-chloro-4-fluorophenyl)amino]-7-[[(3S)-tetrahydro-3-furanyl]oxy]-6-quinazolinyl]-4-(dimethylamino)-(2E)-2-butenamide (Formula-10)

Step-(a):

N-methyl-2-pyrrolidone (200 ml) was added to the compound obtained in example-26 and stirred at 25-30° C. for 15 minutes. Water (400 ml) was added to the reaction mixture and stirred at 25-30° C. for 2 hrs. Filtered the precipitated solid and repeated the process again to get the title compound.

Yield: 90 g.

Step-(b):

Isobutyl acetate (500 ml) was added to the compound obtained in step-(a) and stirred for 15 minutes at the same temperature. Heated the reaction mixture to 80-85° C. Methyl cyclohexane (500 ml) was slowly added to the reaction mixture at 80-85° C. and stirred for 30 minutes at the same temperature. Cooled the reaction mixture to 25-30° C. and stirred for 60 minutes at the same temperature. The solid formed was filtered, washed with isobutyl acetate and dried to get the title compound.

Yield: 75 g; Purity: 99.8% by HPLC; MR: 90-95° C.

Example-30: Preparation of Crystalline Form-R of Compound of Formula-1

A mixture of (S,E)-N-(4-((3-chloro-4-fluoro phenyl)amino)-7-((tetrahydrofuran-3-yl)oxy)quinazolin-6-yl)-4-(dimethylamino)but-2-enamide (5 gms), isobutylacetate (25, ml) and tetrahydrofuran (25 ml) was stirred for 10 minutes at 25-30° C. Filtered the reaction mixture through hyflow bed and washed with a mixture of isobutyl acetate and tetrahydrofuran.

A mixture of malic acid (2.52 gms), isobutyl acetate (7.5 ml) and tetrahydrofuran (7.5 ml) was seeded with crystalline form-R of Afatinib dimaleate. The obtained filtrate was slowly added to the reaction mixture at 25-30° C. and stirred for 20 minutes. Water (1 ml) was added to the reaction mixture at 25-30° C. and stirred for 3 hours at the same temperature. Filtered the precipitated solid, washed with a mixture of isobutyl acetate and tetrahydrofuran and dried to get the title compound.

Yield: 17.5 gms.

The PXRD of the obtained compound is shown in FIG. 12.

Example-31: Preparation of Crystalline Form-R of Compound of Formula-1

A mixture of (S,E)-N-(4-((3-chloro-4-fluoro phenyl)amino)-7-((tetrahydrofuran-3-yl)oxy)quinazolin-6-yl)-4-(dimethylamino)but-2-enamide (5 gms), isobutylacetate (25 ml) and isopropanol (25 ml) was stirred for 10 minutes at 25-30° C. Filtered the reaction mixture through hyflow bed and washed with a mixture of isobutyl acetate and isopropanol.

A mixture of malic acid (2.52 gms), isobutyl acetate (7.5 ml) and isopropanol (7.5 ml) was seeded with crystalline form-R of Afatinib dimaleate. The obtained filtrate was slowly added to the reaction mixture at 25-30° C. and stirred for 20 minutes. Water (2 ml) was added to the reaction mixture at 25-30° C. and stirred for 3 hours at the same temperature. Filtered the precipitated solid, washed with a mixture of isobutyl acetate and isopropanol and dried to get the title compound.

Yield: 17.5 gms.

The PXRD of the obtained compound is shown in FIG. 12.

Example-32: Preparation of Crystalline Form-R of Compound of Formula-1

A mixture of (S,E)-N-(4-((3-chloro-4-fluoro phenyl)amino)-7-((tetrahydrofuran-3-yl)oxy)quinazolin-6-yl)-4-(dimethylamino)but-2-enamide (15 gms), isobutylacetate (75 ml) and 2-methyl tetrahydrofuran (75 ml) was stirred for 10 minutes at 25-30° C. Filtered the reaction mixture through hyflow bed and washed with a mixture of isobutyl acetate and 2-methyl tetrahydrofuran.

A mixture of malic acid (1 gm), isobutyl acetate (37.5 ml) and 2-methyl tetrahydrofuran (37.5 ml) was seeded with crystalline form-R of Afatinib dimaleate. The obtained filtrate was slowly added to the reaction mixture at 25-30° C. and stirred for 20 minutes. Water (3 ml) was added to the reaction mixture at 25-30° C. and stirred for 3 hours at the same temperature. Filtered the precipitated solid, washed with a mixture of isobutyl acetate and 2-methyl tetrahydrofuran and dried to get the title compound.

Yield: 18.0 gms.

The PXRD of the obtained compound is shown in FIG. 12.

Example-33: Preparation of Crystalline Form-R of Compound of Formula-1

A mixture of (S,E)-N-(4-((3-chloro-4-fluoro phenyl)amino)-7-((tetrahydrofuran-3-yl)oxy)quinazolin-6-yl)-4-(dimethylamino)but-2-enamide (2 gms), isobutylacetate (30 ml) and nitro methane (30 ml) was stirred for 10 minutes at 25-30° C. Filtered the reaction mixture through hyflow bed and washed with a mixture of isobutyl acetate and nitromethane. The obtained filtrate was seeded with crystalline form-R of Afatinib dimaleate. Malic acid (1.0 gms) was added to the reaction mixture at 25-30° C. and stirred for 40 minutes at the same temperature. Water (0.4 ml) was added to the reaction mixture and stirred for 3 hours at the same temperature. Filtered the precipitated solid, washed with mixture of isobutyl acetate, nitromethane and dried to get the title compound.

Yield: 2.2 gms.

The PXRD of the obtained compound is shown in FIG. 12.

Example-34: Preparation of Crystalline Form-R of Compound of Formula-1

A mixture of (S,E)-N-(4-((3-chloro-4-fluoro phenyl)amino)-7-((tetrahydrofuran-3-yl)oxy)quinazolin-6-yl)-4-(dimethylamino)but-2-enamide (2 gms), isobutylacetate (30 ml) and nitro methane (30 ml) was stirred for 10 minutes at 25-30° C. Filtered the reaction mixture through hyflow bed and washed with a mixture of isobutyl acetate and nitromethane.

A mixture of malic acid (1 gm), isobutyl acetate (5 ml) and nitromethane (5 ml) was seeded with crystalline form-R of Afatinib dimaleate. The obtained filtrate was slowly added to the reaction mixture at 25-30° C. and stirred for 20 minutes. Water (0.4 ml) was added to the reaction mixture at 25-30° C. and stirred for 3 hours at the same temperature. Filtered the precipitated solid, washed with a mixture of isobutyl acetate, nitromethane and dried to get the title compound.

Yield: 2.4 gms.

The PXRD of the obtained compound is shown in FIG. 12.

Example-35: Preparation of Crystalline Form-R of Compound of Formula-1

A mixture of (S,E)-N-(4-((3-chloro-4-fluoro phenyl)amino)-7-((tetrahydrofuran-3-yl)oxy)quinazolin-6-yl)-4-(dimethylamino)but-2-enamide (25 gms), isobutylacetate (125 ml) and isopropanol (125 ml) was stirred for 15 minutes at 25-30° C. Carbon (1.25 gm) was added to the reaction mixture at 25-30° C. and stirred for 15 minutes. Filtered the reaction mixture through hyflow bed and washed the bed with a mixture of isobutyl acetate and isopropanol.

A mixture of malic acid (12.6 gms), isobutyl acetate (62.5 ml) and isopropanol (62.5 ml) was seeded with crystalline form-R of Afatinib dimaleate. The above obtained filtrate was slowly added to the reaction mixture at 25-30° C. and stirred for 45 minutes. Water (7.5 ml) was added to the reaction mixture at 25-30° C. and stirred for 22 hours at the same temperature. Filtered the precipitated solid, washed with a mixture of isobutyl acetate and isopropanol and dried to get the title compound.

Yield: 32.2 gms; Purity: 99.62% by HPLC.

The PXRD of the obtained compound is shown in FIG. 12.

Example-36: Preparation of Crystalline Form-R of Compound of Formula-1

A mixture of (S,E)-N-(4-((3-chloro-4-fluoro phenyl) amino)-7-((tetrahydrofuran-3-yl)oxy)quinazolin-6-yl)-4-(dimethylamino)but-2-enamide (25 gms), isobutylacetate (125 ml) and isopropanol (125 ml) was stirred for 15 minutes at 25-30° C. Carbon (1.25 gm) was added to the reaction mixture at 25-30° C. and stirred for 15 minutes. Filtered the reaction mixture through hyflow bed and washed the bed with mixture of isobutyl acetate and isopropanol.

A mixture of malic acid (12.6 gms), isobutyl acetate (62.5 ml) and isopropanol (62.5 ml) was stirred for 15 minutes at 25-30° C. The above obtained filtrate was slowly added to the reaction mixture containing malic acid at 25-30° C. and stirred for 45 minutes. Water (7.5 ml) was added to the reaction mixture at 25-30° C. and stirred for 22 hours at the same temperature. Filtered the precipitated solid, washed with a mixture of isobutyl acetate and isopropanol and dried to get the title compound.

Yield: 35 gms; Purity: 99.9% by HPLC.

The PXRD of the obtained compound is shown in FIG. 12.

We claim:

1. Crystalline form-R of Afatinib dimaleate of formula-1

Formula-1

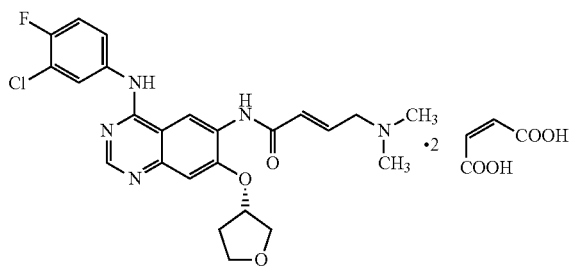

characterized by powder X-ray diffraction peaks at 6.7±0.2° 2θ and 8.8±0.2° 2θ, and two or more peaks selected from the group consisting of 11.7±0.2° 2θ, 13.4±0.2° 2θ, 18.7±0.2° 2θ, 21.9±0.2° 2θ, 24.5±0.2° 2θ, and 27.1±0.2° 2θ.

2. A process for the preparation of crystalline form-R of Afatinib dimaleate of formula-1, Formula-1

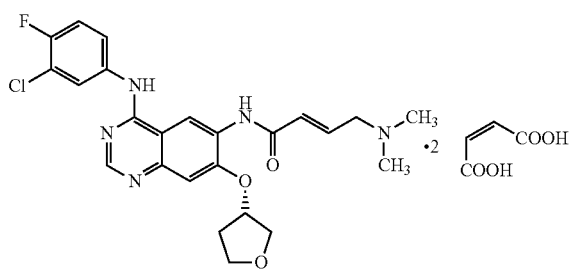

comprising:

a) adding a suitable solvent to N-[4-[(3-chloro-4-fluorophenyl)amino]-7-[[(3S)-tetrahydro-3-furanyl]oxy]-6-quinazolinyl]-4-(dimethylamino)-(2E)-2-butenamide compound of formula-10, Formula-10

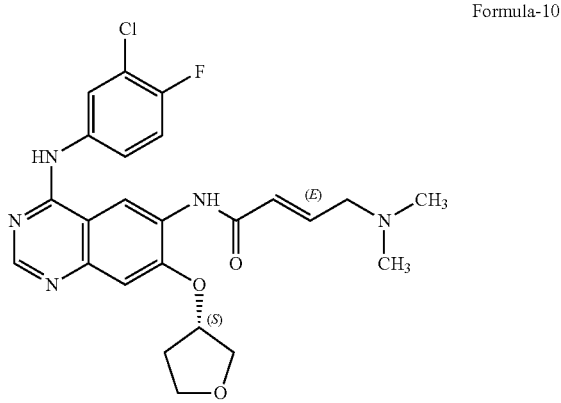

b) adding a suitable solvent to maleic acid, c) optionally, adding seeded crystals of crystalline form-R of compound of formula-1 to the mixture obtained in step-b), d) combining the mixture obtained in step-a) with the mixture obtained in step-b) or step-c), e) adding water to the mixture obtained in step-d), and f) filtering and then drying to get crystalline form-R of Afatinib dimaleate of formula-1.

3. The process according to claim 2, wherein the suitable solvent used in step-a) and step-b) is selected from the group consisting of ester solvents, ether solvents, chloro solvents, hydrocarbon solvents, ketone solvents, polar aprotic solvents alcohol solvents and a mixture thereof.

4. The process for the preparation of crystalline form-R according to claim 2, wherein the process comprises:

a) adding a mixture of isopropanol and isobutyl acetate to compound of formula-10, b) adding a mixture of isopropanol and isobutyl acetate to maleic acid, c) adding seeded crystals of crystalline form-R of compound of formula-1 to the mixture obtained in step b), d) combining the mixture obtained in step-a) with the mixture obtained in step-c), e) adding water to the mixture obtained in step-d), and f) filtering and then drying to get crystalline form-R of Afatinib dimaleate of formula-1.

5. A process for the preparation of crystalline form-R of claim 1, comprising:

a) adding isobutyl acetate and nitromethane to compound of formula-1, b) heating the mixture at 60° C. for 1 hr, c) cooling the mixture to 40° C., and d) filtering the solid and then drying to get crystalline form-R of Afatinib dimaleate of formula-1.

6. The process according to claim 2, wherein the process for the preparation of compound of formula-10,

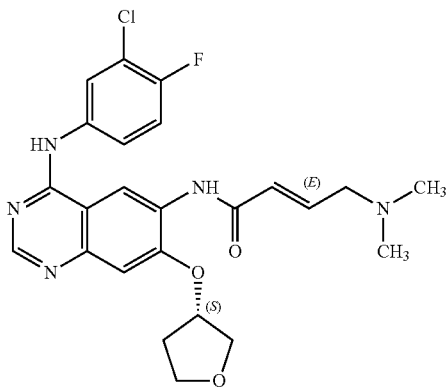

Formula-10 comprises:
a) converting (E)-4-(dimethylamino)but-2-enoic acid compound of formula-9 or its salts

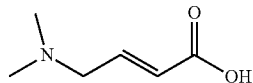

Formula-9 into its acid chloride by using a suitable chlorinating agent in a suitable solvent, and
b) reacting the 4-[(3-Chloro-4-fluorophenyl)amino]-6-amino-7-((S)tetrahydrofuran-3-yloxy)-quinazoline dihydrochloride compound of formula-8a

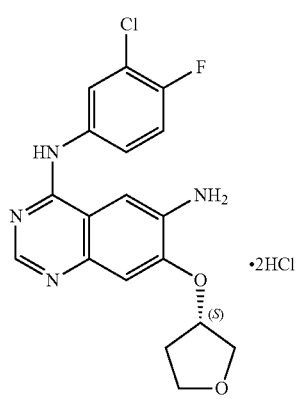

Formula-8a with the acid chloride compound of formula-9 obtained in step-a) in presence or absence of a suitable base in a suitable solvent to provide N-[4-[(3-chloro-4-fluorophenyl)amino]-7-[[(3S)-tetrahydro-3-furanyl]oxy]-6-quinazolinyl]-4-(dimethylamino)-(2E)-2-butenamide compound of formula-10, optionally purifying from a suitable solvent or mixture of solvents to provide N-[4-[(3-chloro-4-fluorophenyl)amino]-7-[[(3S)-tetrahydro-3-furanyl]oxy]-6-quinazolinyl]-4-(dimethylamino)-(2E)-2-butenamide compound of formula-10.

7. The process according to claim 6, wherein
in step-a) and step-b) the suitable solvent is selected from the group consisting of ester solvents, ether solvents, chloro solvents, hydrocarbon solvents, polar aprotic solvents, ketone solvents, alcohol solvents and a mixture thereof;

in step-a) the suitable chlorinating agent is selected from the group consisting of oxalyl chloride, thionyl chloride, phosphorous oxy chloride, phosphorous trichloride, and phosphorous penta chloride; and
in step-b) the suitable base is selected from organic base or inorganic base.

8. The process according to claim 6, wherein the process comprises:
a) converting (E)-4-(dimethylamino)but-2-enoic acid hydrochloride compound of formula-9a

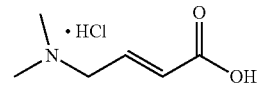

Formula-9a into its acid chloride by using oxalyl chloride in acetonitrile and N,N-dimethylformamide, and
b) reacting the compound of formula-8a with the acid chloride of compound of formula-9a obtained in step-a) in N-methyl-2-pyrrolidone followed by purifying the obtained compound using isobutyl acetate and methyl cyclohexane provides N-[4-[(3-chloro-4-fluorophenyl)amino]-7-[[(3S)-tetrahydro-3-furanyl]oxy]-6-quinazolinyl]-4-(dimethylamino)-(2E)-2-butenamide compound of formula-10.

9. The process according to claim 6, wherein the process for the preparation of 4-[(3-Chloro-4-fluorophenyl) amino]-6-amino-7-((S)tetrahydrofuran-3-yloxy)-quinazoline dihydrochloride compound of formula-8a,

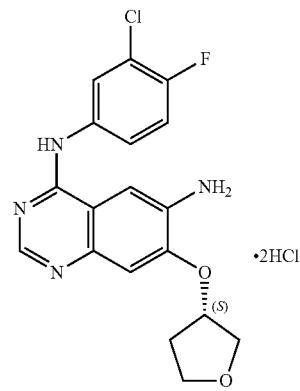

Formula-8a comprises:
a) treating 7-flouro-6-nitroquinazolin-4(3H)-one compound of formula-2

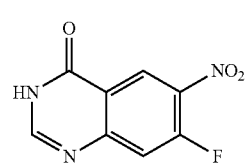

Formula-2 with a suitable chlorinating agent in presence of a suitable base in a suitable solvent to provide 4-chloro-7-fluoro-6-nitroquinazoline compound of formula-3,

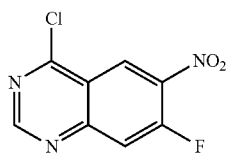

Formula-3 b) reacting compound of formula-3 in-situ with 3-chloro-4-fluoroaniline compound of formula-4

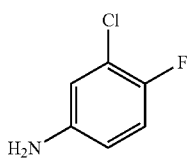

Formula-4 in presence of a suitable base in a suitable solvent to provide N-(3-chloro-4-fluorophenyl)-7-fluoro-6-nitro-quinazolin-4-amine compound of formula 5, optionally purifying from a suitable solvent to provide N-(3-chloro-4-fluorophenyl)-7-fluoro-6-nitroquinazolin-4-amine compound of formula-5,

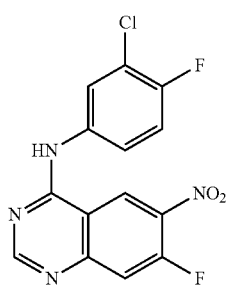

Formula-5 c) reacting compound of formula-5 with (S)-tetrahydrofuran-3-ol compound of formula-6

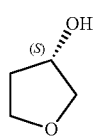

Formula-6 in presence of a suitable base in a suitable solvent to provide (S)—N-(3-chloro-4-fluorophenyl)-6-nitro-7-((tetrahydrofuran-3-yl)oxy)quinazolin-4-amine compound of formula-7,

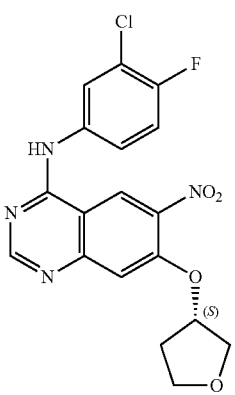

Formula-7 d) treating compound of formula-7 with a suitable reducing agent in a suitable solvent or mixture of solvents, optionally isolating 4-[(3-Chloro-4-fluorophenyl)amino]-6-amino-7-((S)-tetrahydrofuran-3-yloxy)-quinazoline compound of formula-8,

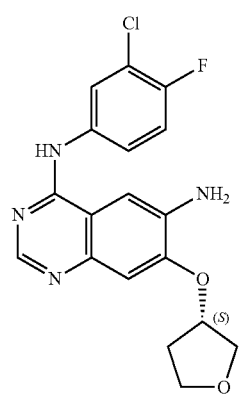

Formula-8 further treating the obtained compound with isopropanolic-HCl provides compound of formula-8a, and e) optionally, purifying the obtained compound of formula-8a with a suitable solvent or mixture of solvents to provide compound of formula-8a.

10. The process according to claim 9, wherein
in step-a) to step-e) the suitable solvent is selected from the group consisting of ester solvents, ether solvents, chloro solvents, hydrocarbon solvents, polar aprotic solvents, ketone solvents, alcohol solvents and a mixture thereof;
in step-a) the suitable chlorinating agent is selected from the group consisting of oxalyl chloride, thionyl chloride, phosphorous oxy chloride, phosphorous trichloride, and phosphorous penta chloride;
in step-a) to c) the suitable base is selected from organic base or inorganic base; and
in step-d) the suitable reducing agent is iron in presence of acetic acid.

11. The process according to claim 9, wherein the process comprises:
a) treating 7-flouro-6-nitroquinazolin-4(3H)-one compound of formula-2 with phosphorous oxychloride in presence of triethylamine in acetonitrile provides 4-chloro-7-fluoro-6-nitroquinazoline compound of formula-3,
b) reacting compound of formula-3 in-situ with 3-chloro-4-fluoroaniline compound of formula-4 in acetonitrile provides N-(3-chloro-4-fluorophenyl)-7-fluoro-6-nitroquinazolin-4-amine compound of formula-5, further purifying the obtained compound using 1,4-dioxane to provide N-(3-chloro-4-fluorophenyl)-7-fluoro-6-nitroquinazolin-4-amine compound of formula-5,
c) reacting compound of formula-5 with (S)-tetrahydrofuran-3-ol compound of formula-6 in presence of potassium tert-butoxide in N-methyl-2-pyrrolidone provides (S)—N-(3-chloro-4-fluorophenyl)-6-nitro-7-((tetrahydrofuran-3-yl)oxy)quinazolin-4-amine compound of formula-7,
d) treating compound of formula-7 with iron powder in presence of acetic acid in a mixture of tetrahydrofuran and water provides 4-[(3-Chloro-4-fluorophenyl)amino]-6-amino-7-((S)-tetrahydrofuran-3-yloxy)-quinazoline compound of formula-8, which on in-situ treating with isopropanolic-HCl provides 4-[(3-Chloro-4-fluorophenyl)amino]-6-amino-7-((S)tetrahydrofuran-3-yloxy)-quinazoline dihydrochloride compound of formula-8a, and e) purifying the compound of formula-8a in a mixture of isopropanol and methanol provides compound of formula-8a.

12. The process according to step-d) of claim 11, wherein the compound of formula-8a is obtained as crystalline solid.

13. The process according to claim 12, wherein the crystalline solid is crystalline form-M and is characterized by its powder X-ray diffraction pattern having peaks at 5.3, 5.7, 5.9, 9.0, 10.4, 11.5, 13.2, 13.4, 13.9, 15.3, 17.3, 18.6, 19.0, 19.4, 20.1, 20.6, 21.4, 22.1, 22.5, 24.1, 24.6, 25.9, 26.1, 26.6, 27.0, 28.5, 30.3, 31.2 and 33.2±0.2 degrees of 2-theta as shown in FIG. 10.

14. A process for the preparation of crystalline form-M according to claim 13, wherein in the process comprises:
   a) treating the (S)—N-(3-chloro-4-fluorophenyl)-6-nitro-7-((tetrahydrofuran-3-yl)oxy)quinazolin-4-amine compound of formula-7 with iron in presence of acetic acid,
   b) adding ethylacetate and stirring the mixture,
   c) basifying the mixture with aqueous sodium carbonate solution,
   d) filtering the mixture,
   e) separating both the aqueous and organic layers,
   f) treating the organic layer with isopropanolic-HCl at 0-10° C., and
   g) filtering the precipitated solid provides the crystalline form-M of 4-[(3-Chloro-4-fluorophenyl)amino]-6-amino-7-((S)tetrahydrofuran-3-yloxy)-quinazoline dihydrochloride compound of formula-8a.

15. The process according to step-e) of claim 11, wherein the compound of formula-8a is obtained as crystalline solid.

16. The process according to claim 15, wherein the crystalline solid is crystalline form-N and is characterized by its powder X-ray diffraction pattern having peaks at 5.4, 6.9, 9.2, 10.4, 10.9, 12.0, 13.9, 14.6, 15.7, 16.5, 18.4, 19.1, 20.3, 20.5, 20.9, 21.8, 22.2, 23.1, 23.8, 25.0, 25.5, 26.1, 26.3, 27.0, 27.3, 27.9, 28.7, 29.8, 31.3, 31.6, 32.8 and 35.0±0.2 degrees of 2-theta as shown in FIG. 11.

17. A process for the preparation of crystalline form-N according to claim 16, wherein in the process comprises:
   a) adding isopropanol and methanol to 4-[(3-chloro-4-fluorophenyl)amino]-6-amino-7-((S)-tetrahydrofuran-3-yloxy)-quinazoline dihydrochloride compound of formula-8a,
   b) stirring the mixture at 25-35° C.,
   c) heating the mixture to 55-65° C.,
   d) cooling the mixture to 0-10° C., and
   e) filtering the solid, washing with isopropanol and then drying to get crystalline form-N of 4-[(3-Chloro-4-fluorophenyl)amino]-6-amino-7-((S)tetrahydrofuran-3-yloxy)-quinazoline dihydrochloride compound of formula-8a.

18. A process for the preparation of crystalline form-R of compound of formula-1,

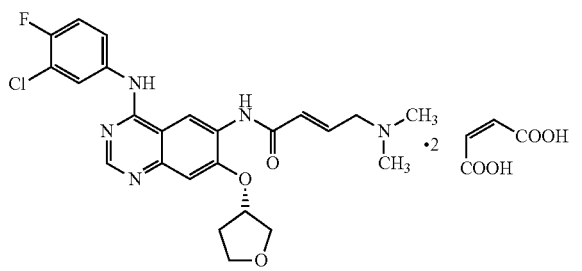

Formula-1 comprising:
a) treating 7-flouro-6-nitroquinazolin-4(3H)-one compound of formula-2

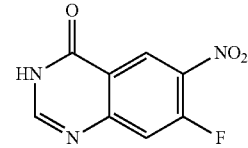

Formula-2 with phosphorous oxychloride in presence of triethylamine in acetonitrile provides 4-chloro-7-fluoro-6-nitroquinazoline compound of formula-3,

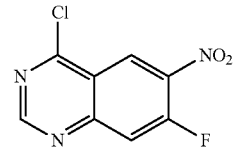

Formula-3 b) reacting the compound of formula-3 in-situ with 3-chloro-4-fluoroaniline compound of formula-4

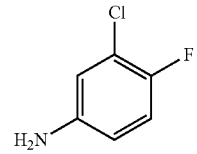

Formula-4 in acetonitrile provides N-(3-chloro-4-fluorophenyl)-7-fluoro-6-nitroquinazolin-4-amine compound of formula-5, further purifying the obtained compound using 1,4-dioxane to provide N-(3-chloro-4-fluorophenyl)-7-fluoro-6-nitroquinazolin-4-amine compound of formula-5,

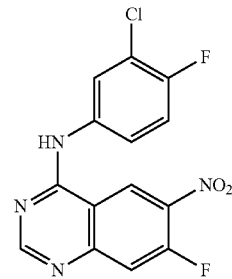

Formula-5 c) reacting compound of formula-5 with (S)-tetrahydrofuran-3-ol compound of formula-6

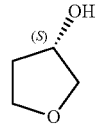

Formula-6 in presence of potassium tert-butoxide in N-methyl-2-pyrrolidone provides (S)—N-(3-chloro-4-fluorophenyl)-6-nitro-7-((tetrahydrofuran-3-yl)oxy)quinazolin-4-amine compound of formula-7, Formula-7

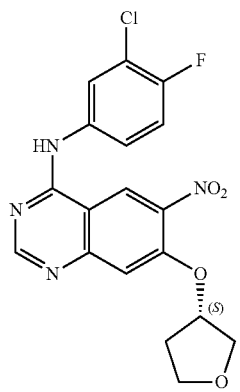

d) treating compound of formula-7 with iron powder in presence of acetic acid in a mixture of tetrahydrofuran and water provides 4-[(3-Chloro-4-fluorophenyl) amino]-6-amino-7-((S)-tetrahydrofuran-3-yloxy)-quinazoline compound of formula-8, Formula-8

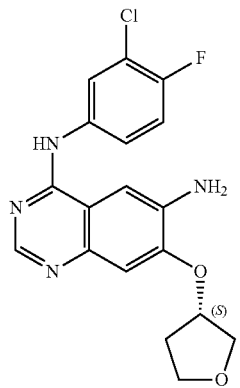

which on in-situ treating with isopropanolic-HCl provides 4-[(3-Chloro-4-fluorophenyl) amino]-6-amino-7-((S)tetrahydrofuran-3-yloxy)-quinazoline dihydrochloride compound of formula-8a, Formula-8a

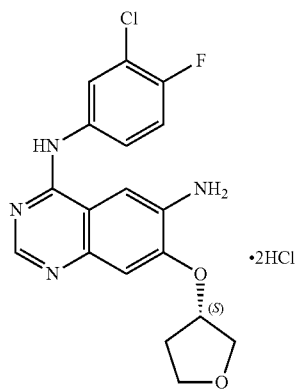

e) purifying the compound of formula-8a in a mixture of isopropanol and methanol provides compound of formula-8a, f) converting (E)-4-(dimethylamino)but-2-enoic acid hydrochloride compound of formula-9a Formula-9a

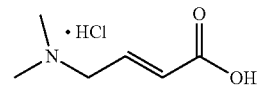

into its acid chloride by using oxalyl chloride in acetonitrile and N,N-dimethylformamide, g) reacting the compound of formula-8a obtained from step-e) with the acid chloride of compound of formula-9a obtained in step-f) in N-methyl-2-pyrrolidone provides N-[4-[(3-chloro-4-fluorophenyl)amino]-7-[[(3 S)-tetrahydro-3-furanyl]oxy]-6-quinazolinyl]-4-(dimethylamino)-(2E)-2-butenamide compound of formula-10, and Formula-10

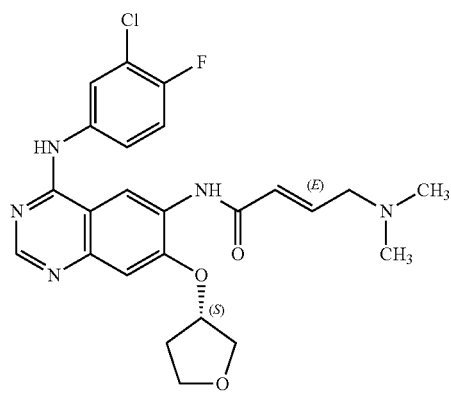

h) treating the N-[4-[(3-chloro-4-fluorophenyl)amino]-7-[[(3S)-tetrahydro-3-furanyl]oxy]-6-quinazolinyl]-4-(dimethylamino)-(2E)-2-butenamide with maleic acid in isopropanol and isobutyl acetate followed by adding water to get crystalline form-R of Afatinib dimaleate of formula-1.

19. The crystalline form-R of Afatinib dimaleate of formula-1 according to claim 1 having purity more than 99% by HPLC.

20. A pharmaceutical composition comprising crystalline Form-R of Afatinib dimaleate of formula-1 according to claim 1 and a pharmaceutically acceptable carrier.

* * * * *